(12) United States Patent
Li et al.

(10) Patent No.: US 7,844,331 B2
(45) Date of Patent: Nov. 30, 2010

(54) METHOD AND APPARATUS FOR CONTROLLING ANTI-TACHYARRHYTHMIA PACING USING HEMODYNAMIC SENSOR

(75) Inventors: Dan Li, Shoreview, MN (US); Gerrard M. Carlson, Champlin, MN (US); Stephen J. Hahn, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 563 days.

(21) Appl. No.: 11/312,082

(22) Filed: Dec. 20, 2005

(65) Prior Publication Data
US 2007/0142866 A1 Jun. 21, 2007

(51) Int. Cl.
*A61N 1/365* (2006.01)
(52) U.S. Cl. .......................... 607/14; 607/24; 600/513
(58) Field of Classification Search ................ 600/486, 600/500, 510; 607/4, 17, 23, 50, 14–15
See application file for complete search history.

(56) References Cited

U.S. PATENT DOCUMENTS

| | | | | |
|---|---|---|---|---|
| 4,137,910 A | * | 2/1979 | Murphy | 600/513 |
| 4,774,950 A | * | 10/1988 | Cohen | 607/6 |
| 4,830,006 A | | 5/1989 | Haluska et al. | |
| 5,163,429 A | | 11/1992 | Cohen | |
| 5,183,040 A | * | 2/1993 | Nappholz et al. | 607/4 |
| 5,282,840 A | | 2/1994 | Hudrlik et al. | |
| 5,311,874 A | | 5/1994 | Baumann et al. | |
| 5,330,505 A | | 7/1994 | Cohen | |
| 5,431,685 A | * | 7/1995 | Alt | 607/6 |
| 5,788,717 A | | 8/1998 | Mann et al. | |
| 5,797,395 A | * | 8/1998 | Martin | 600/486 |
| 5,897,575 A | * | 4/1999 | Wickham | 607/4 |
| 5,978,707 A | | 11/1999 | Krig et al. | |
| 5,999,854 A | | 12/1999 | Deno et al. | |
| 6,044,298 A | * | 3/2000 | Salo et al. | 607/17 |
| 6,101,414 A | | 8/2000 | Kroll | |
| 6,217,525 B1 | | 4/2001 | Medema et al. | |

(Continued)

FOREIGN PATENT DOCUMENTS

EP 0310026 A2 4/1989

(Continued)

OTHER PUBLICATIONS

"Partial International Search Report for Application No. PCT/US2006/043459", (Mar. 14, 2007), 1-6.

(Continued)

*Primary Examiner*—Carl H Layno
*Assistant Examiner*—Luther G Behringer
(74) *Attorney, Agent, or Firm*—Schwegman, Lundberg & Woessner, P.A.

(57) ABSTRACT

A cardiac rhythm management (CRM) system includes an implantable medical device that delivers anti-tachyarrhythmia therapies including anti-tachyarrhythmia pacing (ATP) and at least one hemodynamic sensor that senses a hemodynamic signal. When a tachyarrhythmia episode is detected, the CRM system analyzes the hemodynamic signal to determine whether and/or when to deliver an ATP. In one embodiment, a hemodynamic parameter extracted from the hemodynamic signal is used to predict the potential effectiveness of ATP in terminating the detected tachyarrhythmia episode. In another embodiment, a characteristic feature detected from the hemodynamic signal is used to determine an ATP window during which a delivery of ATP is initiated.

26 Claims, 9 Drawing Sheets

U.S. PATENT DOCUMENTS

| | | | |
|---|---|---|---|
| 6,278,894 B1 | 8/2001 | Salo et al. | |
| 6,314,323 B1 * | 11/2001 | Ekwall | 607/23 |
| 6,493,579 B1 | 12/2002 | Gilkerson et al. | |
| 6,522,914 B1 | 2/2003 | Huvelle | |
| 6,522,925 B1 | 2/2003 | Gilkerson et al. | |
| 6,654,639 B1 | 11/2003 | Lu | |
| 6,708,058 B2 | 3/2004 | Kim et al. | |
| 6,775,572 B2 | 8/2004 | Zhu et al. | |
| 6,873,870 B2 | 3/2005 | Ferek-Petric | |
| 6,885,890 B2 | 4/2005 | Spinelli et al. | |
| 7,010,344 B2 | 3/2006 | Burnes et al. | |
| 7,010,347 B2 | 3/2006 | Schecter | |
| 7,130,681 B2 | 10/2006 | Gebhardt et al. | |
| 7,228,173 B2 | 6/2007 | Cazares | |
| 7,239,915 B2 | 7/2007 | Cohen | |
| 7,277,750 B2 | 10/2007 | Perschbacher et al. | |
| 7,283,871 B1 | 10/2007 | Hofstadter et al. | |
| 7,349,740 B2 * | 3/2008 | Soykan et al. | 607/50 |
| 2003/0083703 A1 | 5/2003 | Zhu et al. | |
| 2003/0204209 A1 | 10/2003 | Burnes et al. | |
| 2003/0208240 A1 | 11/2003 | Pastore et al. | |
| 2004/0215097 A1 | 10/2004 | Wang | |
| 2004/0220634 A1 | 11/2004 | Belk | |
| 2004/0220636 A1 * | 11/2004 | Burnes | 607/17 |
| 2004/0230129 A1 * | 11/2004 | Haefner | 600/510 |
| 2005/0049646 A1 | 3/2005 | Czygan et al. | |
| 2005/0149135 A1 | 7/2005 | Krig et al. | |
| 2005/0222629 A1 | 10/2005 | Perschbacher et al. | |
| 2006/0089675 A1 | 4/2006 | Burnes et al. | |
| 2006/0122651 A1 | 6/2006 | Whitman | |
| 2006/0184060 A1 | 8/2006 | Belalcazar et al. | |
| 2006/0235326 A1 | 10/2006 | Dzwonczyk et al. | |
| 2007/0043394 A1 | 2/2007 | Zhang et al. | |
| 2007/0135848 A1 | 6/2007 | Kim et al. | |
| 2007/0149890 A1 | 6/2007 | Li et al. | |
| 2007/0173894 A1 | 7/2007 | Li | |
| 2007/0197928 A1 | 8/2007 | Kim et al. | |
| 2007/0203524 A1 | 8/2007 | Sheldon et al. | |
| 2008/0281367 A1 | 11/2008 | Zhang et al. | |
| 2009/0318985 A1 | 12/2009 | Shuros et al. | |

FOREIGN PATENT DOCUMENTS

| | | |
|---|---|---|
| EP | 1384433 A1 | 1/2004 |
| EP | 1582233 A3 | 10/2005 |
| WO | WO-9519806 A1 | 7/1995 |
| WO | WO-9520348 A1 | 8/1995 |
| WO | WO-03090858 A1 | 11/2003 |
| WO | WO-2006041337 A1 | 4/2006 |
| WO | WO-2006088805 A2 | 8/2006 |
| WO | WO 2007/078421 * | 7/2007 |
| WO | WO-2007078421 A2 | 7/2007 |
| WO | WO-2007078421 A3 | 7/2007 |
| WO | WO-2008137166 A1 | 11/2008 |

OTHER PUBLICATIONS

Steinbach, K. K., "Hemodynamics during ventriclar tachyarrhythmias", *American Heart Journal*, 127(4 Pt 2), (Apr. 1994), 1102-6.

"PCT Application No. PCT/US2006/043459, International Search Report mailed Oct. 23, 2007", 7 pgs.

"PCT Application No. PCT/US2006/043459, Written Opinion mailed Oct. 23, 2007", 13 pgs.

"European Application Serial No. 06837139.2, Response filed Sep. 1, 2009 to Communication dated Apr. 22, 2009", 15 pgs.

"Japanese Application Serial No. 2008-547229, Amended Claims filed Oct. 26, 2009", (w/English Translation), 10 pgs.

* cited by examiner

METHOD AND APPARATUS FOR CONTROLLING ANTI-TACHYARRHYTHMIA PACING USING HEMODYNAMIC SENSOR

TECHNICAL FIELD

This document relates generally to cardiac rhythm management (CRM) systems and particularly, but not by way of limitation, to a system that controls delivery of anti-tachyarrhythmia pacing (ATP) using one or more hemodynamic sensors.

BACKGROUND

Tachyarrhythmias are abnormal heart rhythms characterized by a rapid heart rate. Tachyarrhythmias generally include supraventricular tachyarrhythmia (SVT, including atrial tachyarrhythmia, AT) and ventricular tachyarrhythmia (VT). Fibrillation is a form of tachyarrhythmia further characterized by an irregular heart rhythm. In a normal heart, the sinoatrial node, the heart's predominant natural pacemaker, generates electrical impulses, called action potentials, that propagate through an electrical conduction system to the atria and then to the ventricles of the heart to excite the myocardial tissues. The atria and ventricles contract in the normal atrio-ventricular sequence and synchrony to result in efficient blood-pumping functions indicated by a normal hemodynamic performance. VT occurs when the electrical impulses propagate along a pathologically formed self-sustaining conductive loop within the ventricles or when a natural pacemaker in a ventricle usurps control of the heart rate from the sinoatrial node. When the atria and the ventricles become dissociated during VT, the ventricles may contract before they are properly filed with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Cardioversion and defibrillation are used to terminate most tachyarrhythmias, including AT, VT, and VF. An implantable cardioverter/defibrillator (ICD) is a cardiac rhythm management (CRM) device that delivers an electric shock to terminate a detected tachyarrhythmia episode by depolarizing the entire myocardium simultaneously and rendering it refractory.

Another type of electrical therapy for tachyarrhythmia is anti-tachyarrhythmia pacing (ATP). In ATP, the heart is competitively paced in an effort to interrupt the reentrant loop causing the tachyarrhythmia. An exemplary ICD includes ATP and defibrillation capabilities so that ATP is delivered to the heart when a non-fibrillation VT is detected, while a defibrillation shock is delivered when fibrillation occurs. Although cardioversion and/or defibrillation are effective in terminating tachyarrhythmia, it consumes a large amount of power and results in patient discomfort owing to the high voltage of the shock pulses. It is desirable, therefore, for the ICD to use ATP to terminate a tachyarrhythmia whenever possible.

The efficacy of ATP in terminating tachyarrhythmia depends on the type of the tachyarrhythmia and the timing of ATP delivery. To be effective, an ATP therapy is to be delivered to the heart during an excitable gap in the reentrant loop. Inaccurate timing of an ATP delivery is known to contribute to the failure in terminating tachyarrhythmia using ATP.

For these and other reasons, there is a need for determining whether and when to deliver an ATP therapy.

SUMMARY

A CRM system includes an implantable medical device that delivers anti-tachyarrhythmia therapies including ATP and at least one hemodynamic sensor that senses a hemodynamic signal. When a tachyarrhythmia episode is detected, the CRM system analyzes the hemodynamic signal to determine whether and/or when to deliver an ATP.

In one embodiment, the CRM system includes a sensing circuit, a tachyarrhythmia detector, a hemodynamic sensor, a hemodynamic parameter detector, a pacing circuit, and a therapy controller. The sensing circuit senses a cardiac signal. The tachyarrhythmia detector detects a tachyarrhythmia episode from the cardiac signal. The hemodynamic sensor senses a hemodynamic signal indicative of hemodynamic performance. The hemodynamic parameter detector detects a hemodynamic parameter from the hemodynamic signal. The pacing circuit delivers pacing pulses. The therapy controller includes a therapy selector and an ATP controller. The therapy selector compares an arrhythmic value of the hemodynamic parameter detected during the tachyarrhythmia episode to a normal range of the hemodynamic parameter. If the arrhythmic value of the hemodynamic parameter falls within the normal range of the hemodynamic parameter, the therapy selector selects an ATP algorithm. The ATP controller controls the delivery of the pacing pulses by executing the selected ATP algorithm.

In another embodiment, a method for operating the CRM system to determine whether to deliver an ATP therapy is provided. A cardiac signal is sensed. A tachyarrhythmia episode is detected from the cardiac signal. A hemodynamic signal indicative of hemodynamic performance is sensed. A hemodynamic parameter is detected from the hemodynamic signal. An arrhythmic value of the hemodynamic parameter is produced as a value of the hemodynamic parameter detected during the tachyarrhythmia episode. The arrhythmic value of the hemodynamic parameter is compared to a normal range of the hemodynamic parameter. If the arrhythmic value of the hemodynamic parameter falls within the normal range of the hemodynamic parameter, the ATP therapy is selected.

In one embodiment, the CRM system includes a sensing circuit, a tachyarrhythmia detector, a hemodynamic sensor, a hemodynamic parameter detector, a pacing circuit, and a therapy controller. The sensing circuit senses a cardiac signal. The tachyarrhythmia detector detects a tachyarrhythmia episode from the cardiac signal. The hemodynamic sensor senses a hemodynamic signal indicative of hemodynamic performance. The pacing circuit delivers pacing pulses. The therapy controller includes a characteristic feature detector and an ATP controller. The characteristic feature detector detects a predetermined type characteristic feature from the hemodynamic signal. The ATP controller times the delivery of the pacing pulses using at least the predetermined type characteristic feature.

In another embodiment, a method for operating the CRM system to time an ATP delivery is provided. A cardiac signal is sensed. A tachyarrhythmia episode is detected from the cardiac signal. A hemodynamic signal indicative of hemodynamic performance is sensed. A predetermined type characteristic feature is detected from the hemodynamic signal. A beginning point of an ATP window is located using at least the predetermined type characteristic feature. The ATP delivery is timed using the beginning point of the ATP window.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

Figure 1:
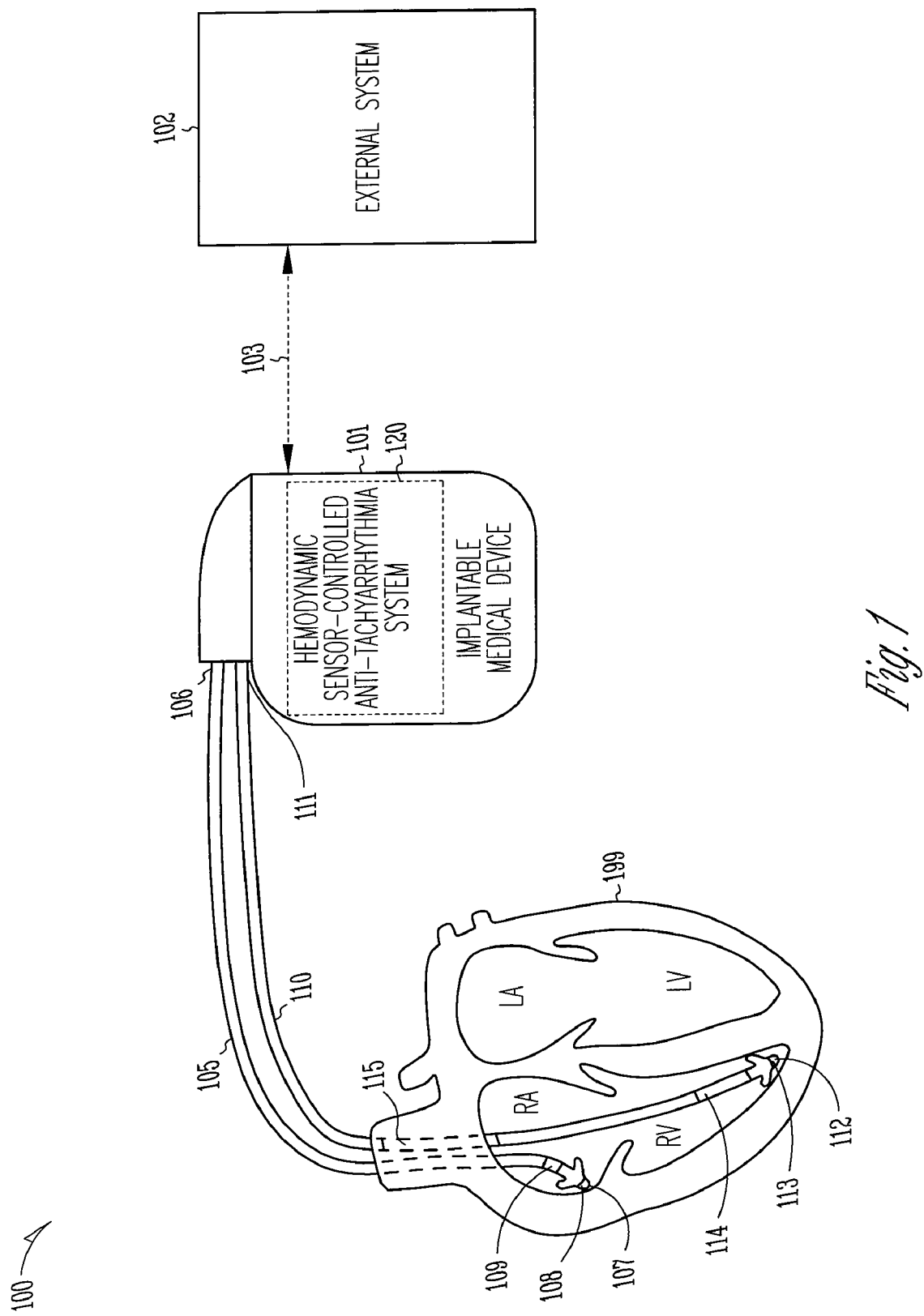
FIG. 1 is an illustration of an embodiment of a CRM system including a hemodynamic sensor-controlled anti-tachyarrhythmia system and portions of the environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

The relationship between a heart rate and a cardiac cycle length (also known as cardiac interval), as used in this document, is the relationship between a frequency and its corresponding period. If a heart rate is given in beats per minute (bpm), its corresponding cardiac cycle length in milliseconds is calculated by dividing 60,000 by the heart rate (where 60,000 is the number of milliseconds in a minute). Any process, such as a comparison, using a heart rate is to be modified accordingly when a cardiac cycle length is used instead. For example, if a tachyarrhythmia is detected when the ventricular rate exceeds a tachyarrhythmia threshold rate, an equivalent process is to detect the tachyarrhythmia when the ventricular cycle length (also known as ventricular interval) falls below a tachyarrhythmia threshold interval. The appended claims should be construed to cover such variations.

This document discusses a CRM system that delivers anti-tachyarrhythmia therapies including ATP and controls the anti-tachyarrhythmia therapies, including selection and delivery time of the ATP, using one or more hemodynamic signals. In one embodiment, the CRM system uses a hemodynamic sensor to sense a hemodynamic signal and detect a hemodynamic parameter from the hemodynamic signal when a tachyarrhythmia episode is being detected. If the value of the hemodynamic parameter detected during the tachyarrhythmia episode falls within a pre-specified range, the CRM system selects the ATP to treat the detected tachyarrhythmia episode. Examples of the hemodynamic signal include a heart sound signal, an arterial pressure signal, and an impedance signal. In one embodiment, the CRM system uses a hemodynamic sensor to sense a hemodynamic signal having a detectable characteristic feature that can be used as a time reference for delivering ATP pulses during the excitable gap in the reentrant loop. Examples of such a detectable characteristic feature in the hemodynamic signal include the peak of second heart sound (S2) in the heart sound signal, the dicrotic notch in the arterial pressure signal, a trough point in the first derivative of the impedance signal, and a zero-crossing point in the second derivative of the impedance signal. In one embodiment, the CRM system uses multiple hemodynamic sensors to sense multiple hemodynamic signals for controlling whether and/or when to deliver the ATP.

FIG. 1 is an illustration of one embodiment of a CRM system 100 and portions of the environment in which CRM system 100 operates. CRM system 100 includes an implantable medical device 101 that is electrically coupled to a heart 199 through leads 105 and 110. An external system 102 communicates with implantable medical device 101 via a telemetry link 103.

Implantable medical device 101 delivers anti-tachyarrhythmia therapies including ATP and cardioversion/defibrillation therapies. In one embodiment, implantable medical device 101 is an implantable cardioverter/defibrillator (ICD) with cardiac pacing capabilities. In another embodiment, in addition to a pacemaker and a cardioverter/defibrillator, implantable medical device 101 further includes one or more of other monitoring and/or therapeutic devices such as a neural stimulator, a drug delivery device, and a biological therapy device. Implantable medical device 101 includes a hermetically sealed can housing an electronic circuit that senses physiological signals and delivers therapeutic electrical pulses. The hermetically sealed can also functions as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is a pacing lead that includes a proximal end 106 connected to implantable medical device 101 and a distal end 107 placed in the right atrium (RA) of heart 199. A pacing-sensing electrode 108 is located at distal end 107. Another pacing-sensing electrode 109 is located near distal end 107. Electrodes 108 and 109 are electronically connected to implantable medical device 101 via separate conductors in lead 105 to allow sensing of the atrial electrogram and/or delivery of atrial pacing pulses. Lead 110 is a defibrillation lead that includes a proximal end 111 connected to implantable medical device 101 and a distal end 112 placed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to implantable medical device 101 via separate conductors in lead 110. Electrode 113 allows sensing of the ventricular electrogram and/or delivery of ventricular pacing pulses. Electrodes 114 and 115 allow delivery of ventricular cardioversion/defibrillation pulses.

Implantable medical device 101 includes a hemodynamic sensor-controlled anti-tachyarrhythmia system 120. One or more implantable hemodynamic sensors are included in, and/or connected to, implantable medical device 101. System 120 uses one or more hemodynamic signals sensed by the one or more implantable hemodynamic sensors to determine whether ATP is a suitable therapy for terminating a detected tachyarrhythmia episode and/or to determine a time for an effective ATP delivery. Various embodiments of system 120 are discussed below, with reference to FIGS. 3, 4, and 6-9.

External system 102 allows for programming of implantable medical device 101 and receives signals acquired by implantable medical device 101. In one embodiment, external system 102 includes a programmer. In another embodiment, external system 102 is a patient management system including an external device in proximity of implantable medical device 101, a remote device in a relatively distant location, and a telecommunication network linking the external device and the remote device. The patient management system allows access to implantable medical device 101 from a remote location, such as for monitoring patient status and adjusting therapies. Telemetry link 103 is a wireless communication link providing for bidirectional data transmission between implantable medical device 101 and external system 102. In one embodiment, telemetry link 103 is an inductive telemetry link. In an alternative embodiment, telemetry link 103 is a far-field radio-frequency telemetry link. Telemetry link 103 provides for data transmission from implantable medical device 101 to external system 102. This may include, for example, transmitting real-time physiological data acquired by implantable medical device 101, extracting physiological data acquired by and stored in implantable medical device 101, extracting therapy history data stored in implantable medical device 101, and extracting data indicating an operational status of implantable medical device 101 (e.g., battery status and lead impedance). Telemetry link 103 also provides for data transmission from external system 102 to implantable medical device 101. This may include, for example, programming implantable medical device 101 to acquire physiological data, programming implantable medical device 101 to perform at least one self-diagnostic test (such as for a device operational status), programming implantable medical device 101 to enable an available monitoring or therapeutic function (such as ATP), and programming implantable medical device 101 to adjust therapeutic parameters such as pacing and/or cardioversion/defibrillation parameters.

Figure 2:
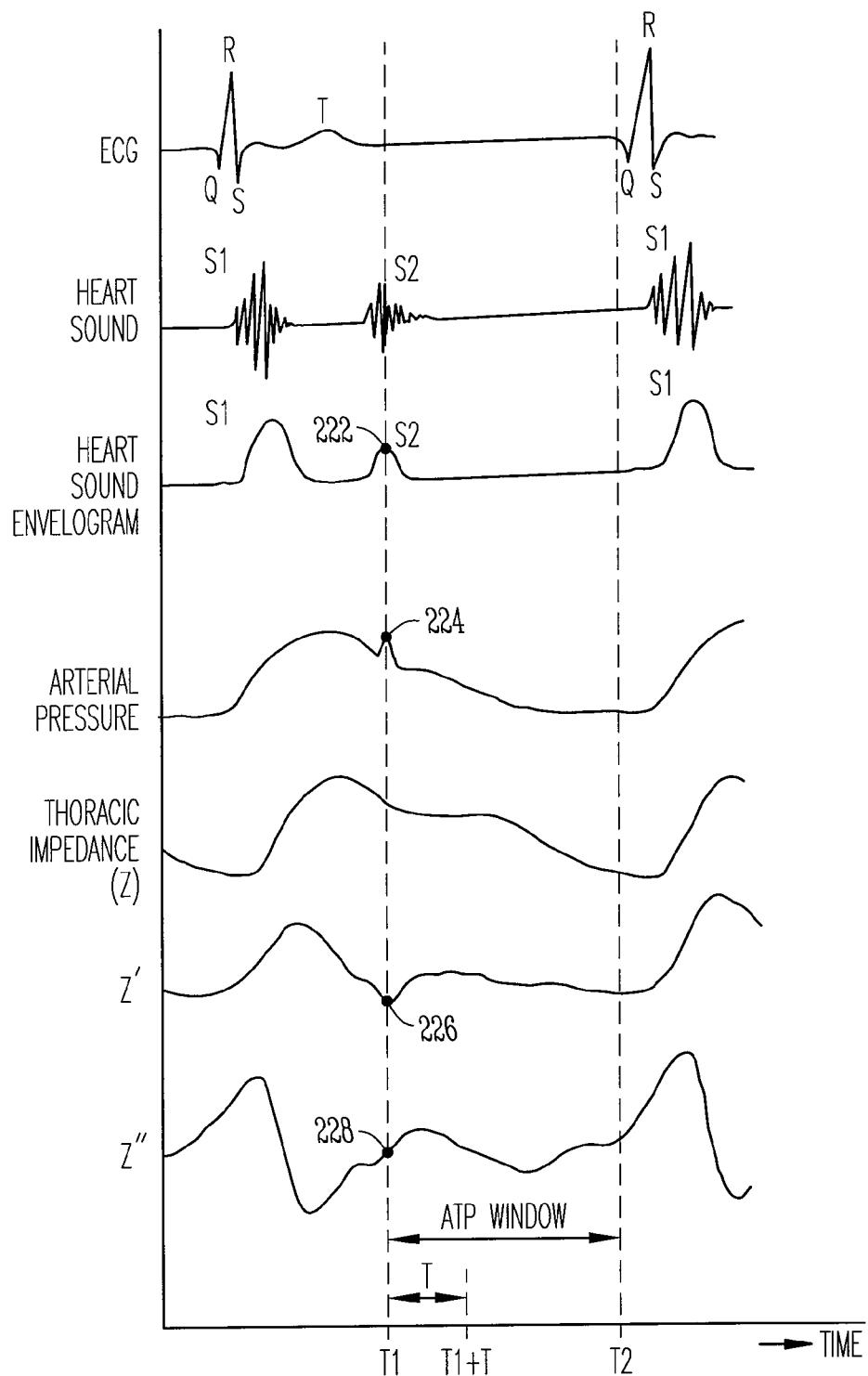
FIG. 2 is an illustration of timing for effective delivery of ATP.

FIG. 2 is an illustration of timing for effective delivery of ATP showing an ATP window and several physiological signals over a portion of a cardiac cycle. To be effective in terminating a detected tachyarrhythmia episode, an ATP therapy is to be delivered during the ATP window, which approximately corresponds to the excitable gap in the reentrant loop.

The excitable gap approximately corresponds to the time from the end of the T wave to the beginning of the next QRS complex. The T wave is a period when the heart is "repolarizing". Most low-amplitude electrical stimulation pulses do not result in cardiac contraction if delivered during the T wave. During VT, it becomes challenging, if not impossible, to reliably detect the T wave. Thus, another measure, such as a hemodynamic measure, is used to indicate the excitable gap. For example, the S2 heart sound corresponds to closure of the aortic valve that signals the end of the ejection phase of a cardiac contraction, which also approximately corresponds to the end of the T wave. Thus, the hemodynamic measure may be used to estimate the end of repolarization, even if the T wave cannot be reliably detected. The hemodynamic measure (such as the S2 heart sound) may also be used to distinguish between VT and VF. During VT, there is still some pumping of blood and hence at least pseudo-normal opening and closing of the valves. However, during VF there is not enough pumping action to open and close the valves. In one embodiment, the discrimination between VT and VF is a factor for determining whether ATP is to be delivered.

The illustrated physiological signal include an electrocardiogram (ECG) and several examples of hemodynamic signals including a heart sound signal, a heart sound envelogram, an arterial pressure signal, an impedance signal (Z), a first derivative of the impedance signal (Z', i.e., dZ/dt), and a second derivative of the impedance signal (Z", i.e., $d^2Z/dt^2$). One or more hemodynamic parameters are extracted from such signals to indicate a patient's hemodynamic state. The hemodynamic state during a detected tachyarrhythmia episode is predictive of the effectiveness of the ATP therapy in terminating that detected tachyarrhythmia episode. In various embodiments, a range of a hemodynamic parameter is pre-specified, such as by sensing the hemodynamic signal during a normal sinus rhythm (NSR) and establishing a range of values considered as indicative of normal hemodynamic performance. This pre-specified range of the hemodynamic parameter is referred to as the "normal range" of the hemodynamic parameter. The ATP is considered appropriate if the value of the hemodynamic parameter detected during the detected tachyarrhythmia episode falls within the normal range. If the value of the hemodynamic parameter detected during the detected tachyarrhythmia episode is outside the normal range, a more aggressive therapy such as a defibrillation shock is considered necessary.

As illustrated in FIG. 2, the ATP window has a beginning point at T1 and an end point at T2. The beginning point is temporally associated with the closure of the aortic valve and the closure of the pulmonary valve during the cardiac cycle. These two valve closures occur soon after the T wave of the ECG signal. Various characteristic features in the hemodynamic signals are associated with the closure of the aortic valve and the closure of the pulmonary valve, therefore being usable for indicating the beginning point (T1) of the ATP window. Such characteristic features include, for example, an S2 peak 222 in the heart sound signal, a dicrotic notch 224 of the arterial pressure signal, a trough point 226 in the first derivative of the impedance signal, and a zero-crossing point 228 in the second derivative of the impedance signal. The end point (T2) of the ATP window occurs before the QRS complex of the next cardiac cycle. In various embodiments, a time interval T starts with the beginning point (T1) of the ATP window, and the delivery of ATP pulses is initiated when time interval T expires (at T1+T).

In one embodiment, the delivery of the ATP therapy includes the delivery of a burst of pacing pulses, with the leading pacing pulse delivered when time interval T expires. In a specific embodiment, the delivery of the ATP therapy includes the delivery of a burst of about 1 to 30 pacing pulses evenly spaced at a pacing interval of about 120 to 750 milliseconds, with the leading pacing pulse delivered at about 0 to 250 milliseconds after the beginning point (T1) of the ATP pacing window. In one embodiment, to account for the heart rate during each specific tachyarrhythmia episode, the pacing interval is set to be a predetermined percentage of measured cardiac cycle length. In a specific embodiment, the predetermined percentage is in a range of approximately 70-95%. The time interval T is chosen such that the delivery of ATP pulses is initiated within the ATP window. In other words, the time interval T is to end before the end point (T2) of the ATP window. In one embodiment, to account for the heart rate during each specific tachyarrhythmia episode, the time interval T is determined as a fraction of the cardiac cycle length estimated for the heart beat during which the delivery of ATP pulses is to be initiated. This cardiac cycle length is estimated, for example, by calculating an average cardiac cycle length using a plurality of ventricular cycle lengths detected before the initiation of the delivery of ATP pulses. In one embodiment, the time interval T is automatically calculated as a predetermined fraction of the estimated cardiac cycle length. In a specific embodiment, the time interval T is calculated to be approximately 15% of the estimated cardiac cycle length.

Figure 3:
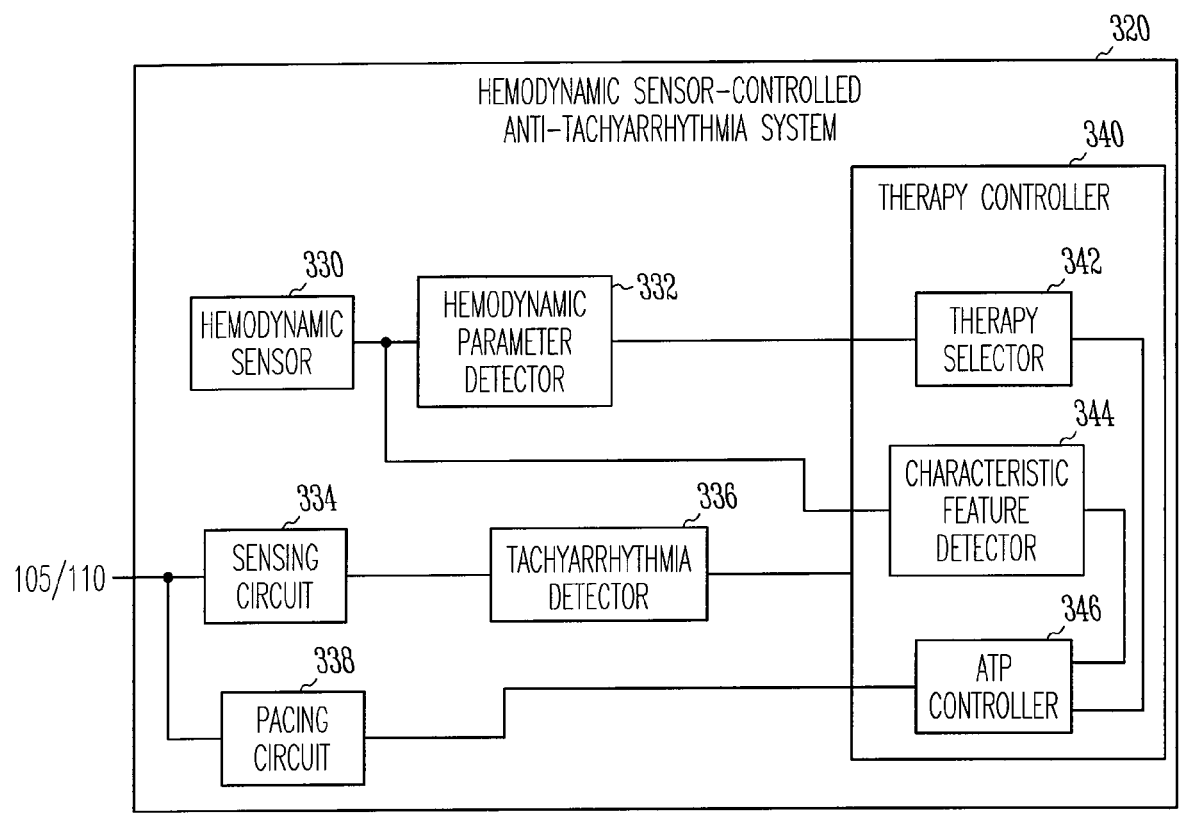
FIG. 3 is a block diagram illustrating an embodiment of the hemodynamic sensor-controlled anti-tachyarrhythmia system.

FIG. 3 is a block diagram illustrating an embodiment of a hemodynamic sensor-controlled anti-tachyarrhythmia system 320, which is a specific embodiment of system 120. System 320 includes a hemodynamic sensor 330, a hemodynamic parameter detector 332, a sensing circuit 334, a tachyarrhythmia detector 336, a pacing circuit 338, and a therapy controller 340.

Hemodynamic sensor 330 senses a hemodynamic signal indicative of hemodynamic performance. Hemodynamic parameter detector 332 detects a hemodynamic parameter from the hemodynamic signal. An arrhythmic value of the hemodynamic parameter detected during a tachyarrhythmia episode indicates whether ATP is considered potentially effective in terminating that tachyarrhythmia episode. The hemodynamic signal also includes a detectable characteristic feature. In one embodiment, the detectable characteristic feature is a morphological feature temporally associated with the closure of the aortic valve and the closure of the pulmonary valve during each cardiac cycle.

Sensing circuit 334 senses one or more cardiac signals using electrodes in leads 105 and/or 110. Tachyarrhythmia detector 336 detects tachyarrhythmia episodes from the one or more cardiac signals.

Pacing circuit 338 delivers pacing pulses through leads 105 and/or 110. Depending on the pacing mode controlled by therapy controller 340, the pacing pulses are delivered for various purposes such as anti-bradyarrhythmia therapy, cardiac resynchronization therapy, cardiac remodeling control therapy, and ATP therapy.

In one embodiment, as illustrated in FIG. 3, therapy controller 340 includes a therapy selector 342, a characteristic feature detector 344, and an ATP controller 346. Therapy selector 342 compares the arrhythmic value of the hemodynamic parameter detected during the tachyarrhythmia episode to a pre-specified normal range of the hemodynamic parameter and selects an ATP algorithm if the arrhythmic value of the hemodynamic parameter falls within the normal range of the hemodynamic parameter. Characteristic feature detector 344 detects a predetermined type characteristic feature from the hemodynamic signal. If the ATP algorithm is selected, ATP controller 346 controls the delivery of the pacing pulses from pacing circuit 338 by executing the selected ATP algorithm, including timing the delivery of the pacing pulses using at least the detected predetermined type characteristic feature.

In other embodiments, therapy controller 340 includes ATP controller 346 and any one of therapy selector 342 and characteristic feature detector 344. In one embodiment, if therapy selector 342 selects the ATP algorithm, ATP controller 346 times the delivery of the ATP pulses using predetermined timing parameters. In another embodiment, if the ATP algorithm is selected according to predetermined criteria such as tachyarrhythmic heart rate (without using the hemodynamic signal), characteristic feature detector 344 detects the predetermined type characteristic feature from the hemodynamic signal, and ATP controller 346 times the delivery of the pacing pulses using at least the detected predetermined type characteristic feature.

Figure 4:
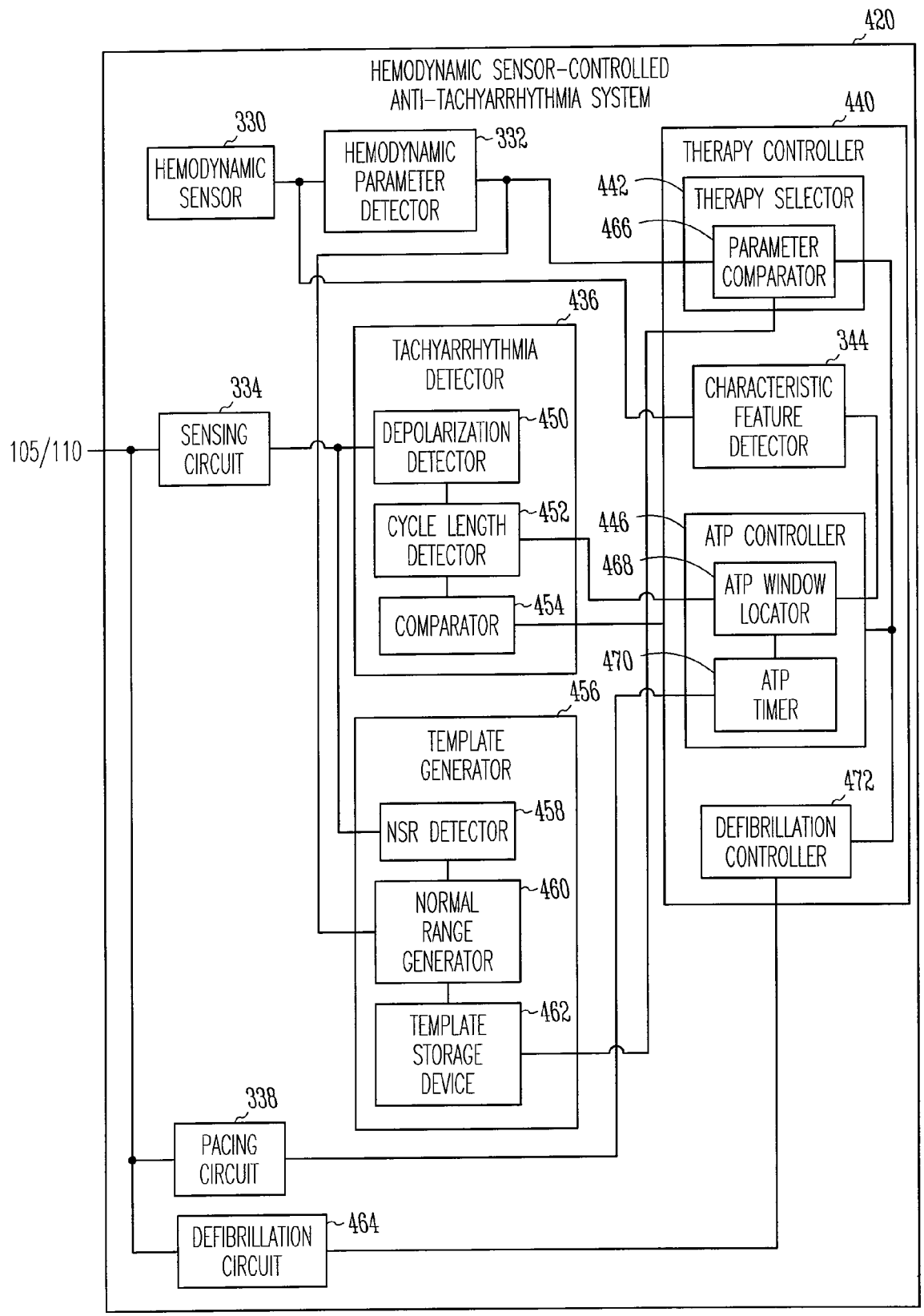
FIG. 4 is a block diagram illustrating a specific embodiment of the hemodynamic sensor-controlled anti-tachyarrhythmia system.

FIG. 4 is a block diagram illustrating an embodiment of a hemodynamic sensor-controlled anti-tachyarrhythmia system 420, which is a specific embodiment of system 320. System 420 includes hemodynamic sensor 330, hemodynamic parameter detector 332, sensing circuit 334, a tachyarrhythmia detector 436, a pacing circuit 338, a defibrillation circuit 464, a template generator 456, and a therapy controller 440.

Tachyarrhythmia detector 436 is a specific embodiment of tachyarrhythmia detector 336 and includes a depolarization detector 450, a cycle-length detector 452, and a comparator 454. Depolarization detector 450 detects cardiac depolarizations from the one or more cardiac signals sensed by sensing circuit 334. Cycle-length detector 452 detects a cardiac cycle length from the one or more cardiac signals. Comparator 454 compares the detected cardiac cycle length to at least one tachyarrhythmia threshold cycle length and indicates a detection of tachyarrhythmia if the detected cardiac cycle length is shorter than the tachyarrhythmia threshold cycle length. In one embodiment, tachyarrhythmia detector 436 detects ventricular tachyarrhythmia (VT). Depolarization detector 450 detects ventricular depolarizations (R waves) from a ventricular electrogram sensed by sensing circuit 334. Cycle-length detector 452 detects ventricular intervals (RR intervals) each being a time interval between two consecutively detected ventricular depolarizations and calculates the cardiac cycle length by averaging a predetermined number of the detected ventricular intervals. In a specific embodiment, the cardiac cycle length detected by cycle-length detector 452 is an average of ventricular intervals of about four consecutive heart beats. Comparator 454 compares the detected cardiac cycle length to a predetermined VT threshold cycle length and indicates a detection of VT when the detected cardiac cycle length drops below the predetermined VT threshold cycle length.

Defibrillation circuit 464 delivers cardioversion/defibrillation pulses through lead 110. System 420 provides anti-tachyarrhythmia therapies including ATP therapy and cardioversion/defibrillation therapy.

Template generator 456 is a specific embodiment of template generator 356 and includes a NSR detector 458, a normal range generator 460, and a template storage device 462. NSR detector 458 detects NSR from the one or more cardiac signals. In one embodiment, NSR detector 458 indicates a detection of NSR when the average value of a plurality of cardiac cycle lengths falls within a predetermined NSR window and a variance of the cardiac cycle lengths is below a predetermined NSR threshold cycle length variance. In a specific embodiment, the average value of the plurality of cardiac cycle lengths is the cardiac cycle length detected by cycle length detector 452, and the variance is calculated from the same ventricular intervals used by cycle length detector 452 for calculating the cardiac cycle length. Normal range generator 460 receives NSR values of the hemodynamic parameter detected while the NSR is detected. Using a plurality of the NSR values of the hemodynamic parameter, normal range detector 460 produces a normal range of the hemodynamic parameter. In one embodiment, normal range generator 460 produces the normal range using the equation:

$$X_{MAX}=|X|_{AVG}+k\cdot|X|_{SD};$$

$$X_{MIN}=|X|_{AVG}-k\cdot|X|_{SD};\qquad [1]$$

where $X_{MAX}$ and $X_{MIN}$ are the boundary values of the normal range, $|X|_{AVG}$ is an average value of the hemodynamic parameter calculated using the plurality of NSR values of the hemodynamic parameter, $|X|_{SD}$ is a standard deviation of the hemodynamic parameter calculated using the plurality of NSR values of the hemodynamic parameter, and k is a predetermined constant. In a specific embodiment, the plurality of NSR values of the hemodynamic parameter includes approximately 15 NSR values of the hemodynamic parameter. Template storage device 462 stores the normal range of the hemodynamic parameter. In one embodiment, template generator 456 regularly updates the stored normal range of the hemodynamic parameter, such as on a periodic basis.

Therapy controller 440 is a specific embodiment of therapy controller 340 and controls the delivery of the pacing from pacing circuit 338 and the delivery of cardioversion/defibrillation pulses from defibrillation circuit 464. Therapy controller 440 includes a therapy selector 442, characteristic feature detector 344, an ATP controller 446, and a defibrillation controller 472.

Therapy selector 442 includes a parameter comparator 466 that compares the arrhythmic value of the hemodynamic parameter detected during the detected tachyarrhythmia episode to the stored normal range of the hemodynamic parameter. If the arrhythmic value of the hemodynamic parameter falls within the stored normal range of the hemodynamic parameter, therapy selector 442 selects the ATP algorithm. If the arrhythmic value of the hemodynamic parameter is out of the stored normal range of the hemodynamic parameter, therapy selector 442 selects a cardioversion/defibrillation algorithm or an ATP-before-charge algorithm. If the ATP algorithm is selected, ATP controller 446 controls the delivery of one or more bursts of ATP pulses from pacing circuit 338. If the ATP fails to terminate the detected tachyarrhythmia episode, defibrillation controller 472 controls the delivery of one or more cardioversion/defibrillation pulses from defibrillation circuit 464 until the detected tachyarrhythmia episode is terminated. If the cardioversion/defibrillation algorithm is selected, defibrillation controller 472 controls the delivery of one or more cardioversion/defibrillation pulses from defibrillation circuit 464 until the detected tachyarrhythmia episode is terminated. If the ATP-before-charge algorithm is selected, ATP controller 446 controls the delivery of one or more bursts of ATP pulses from pacing circuit 338 while defibrillation controller 472 prepares defibrillation circuit 464 for delivering a cardioversion/defibrillation pulse by charging a defibrillation capacitor that stores the energy for the cardioversion/defibrillation pulse. If the ATP fails to terminate the detected tachyarrhythmia episode, defibrillation controller 472 immediately causes the delivery of the cardioversion/defibrillation pulse from defibrillation circuit 464. An example of a system executing such an ATP-before-charge algorithm is discussed in U.S. patent application Ser. No. 10/817,751, entitled "METHOD AND APPARATUS FOR ANTI-TACHYARRHYTHMIA PACING AND DEFIBRILLATION," filed on Apr. 2, 2004, assigned to Cardiac Pacemakers, Inc., which is incorporated by reference herein in its entirety.

ATP controller 446 is a specific embodiment of ATP controller 346 and includes an ATP window locator 468 and an ATP timer 470. ATP window locator 468 locates at least the beginning point (T1) of the ATP window. In one embodiment, ATP window locator 470 also locates the end point (T2) of the ATP window. In one embodiment, ATP window locator 468 selects a predetermined type characteristic feature detected by characteristic feature detector 344 as the beginning point (T1) of the ATP window. In another embodiment, ATP window locator 468 locates the beginning point (T1) of the ATP window using a predetermined type characteristic feature detected by characteristic feature detector 344 and an arrhythmia cycle length being the cardiac cycle length detected by cycle length detector 452 during the detected tachyarrhythmia episode. In a specific embodiment, the beginning point (T1) of the ATP window is the predetermined type characteristic feature or the end of a timing interval in the same cardiac cycle, whichever occurs later, where the timing interval is a predetermined percentage of the arrhythmia cycle length and starts from a detected ventricular depolarization. In another embodiment, ATP window locator 468 locates the beginning point (T1) of the ATP window using a predetermined type characteristic feature detected by characteristic feature detector 344, the arrhythmia cycle length, and a parameter related to a relative stability of the arrhythmic cycle length. In a specific embodiment, ATP window locator 468 assigns more weight to the predetermined type characteristic feature when the degree of the stability of the arrhythmic cycle length decreases. For example, using a ventricular depolarization (R wave) as the time reference (t=0), the beginning point (T1) of the ATP window is given by $$T1=(1-\alpha)\cdot T_{CP}+\alpha\cdot x\%\cdot CL,\qquad [2]$$

where $\alpha$ is the a weighting factor that is related to the relative stability of the arrhythmic cycle length and has a value between 0 and 1, $T_{CP}$ is the time of the predetermined type characteristic feature, x% is a predetermined percentage, and CL is the arrhythmic cycle length. The weighting factor $\alpha$ equals, for example, $e^{-var}$, where var is the variance of the ventricular intervals used to calculate the arrhythmia cycle length. ATP timer 470 times the ATP interval (T) from the beginning point (T1) of the ATP window and initiates the delivery of the ATP pulses when the ATP interval (T) expires. In one embodiment, ATP timer 470 initiates the delivery of the leading pacing pulse of a burst of ATP pulses when the ATP interval (T) expires. The ATP interval is chosen within the ATP window (between T1 and T2). In one embodiment, the end point (T2) of the ATP window in a cardiac cycle is the end of a time interval that starts with a ventricular depolarization (R wave) and has a length being a given percentage of the arrhythmic cycle length. In a specific embodiment, the given percentage is about 95%.

Figure 5:
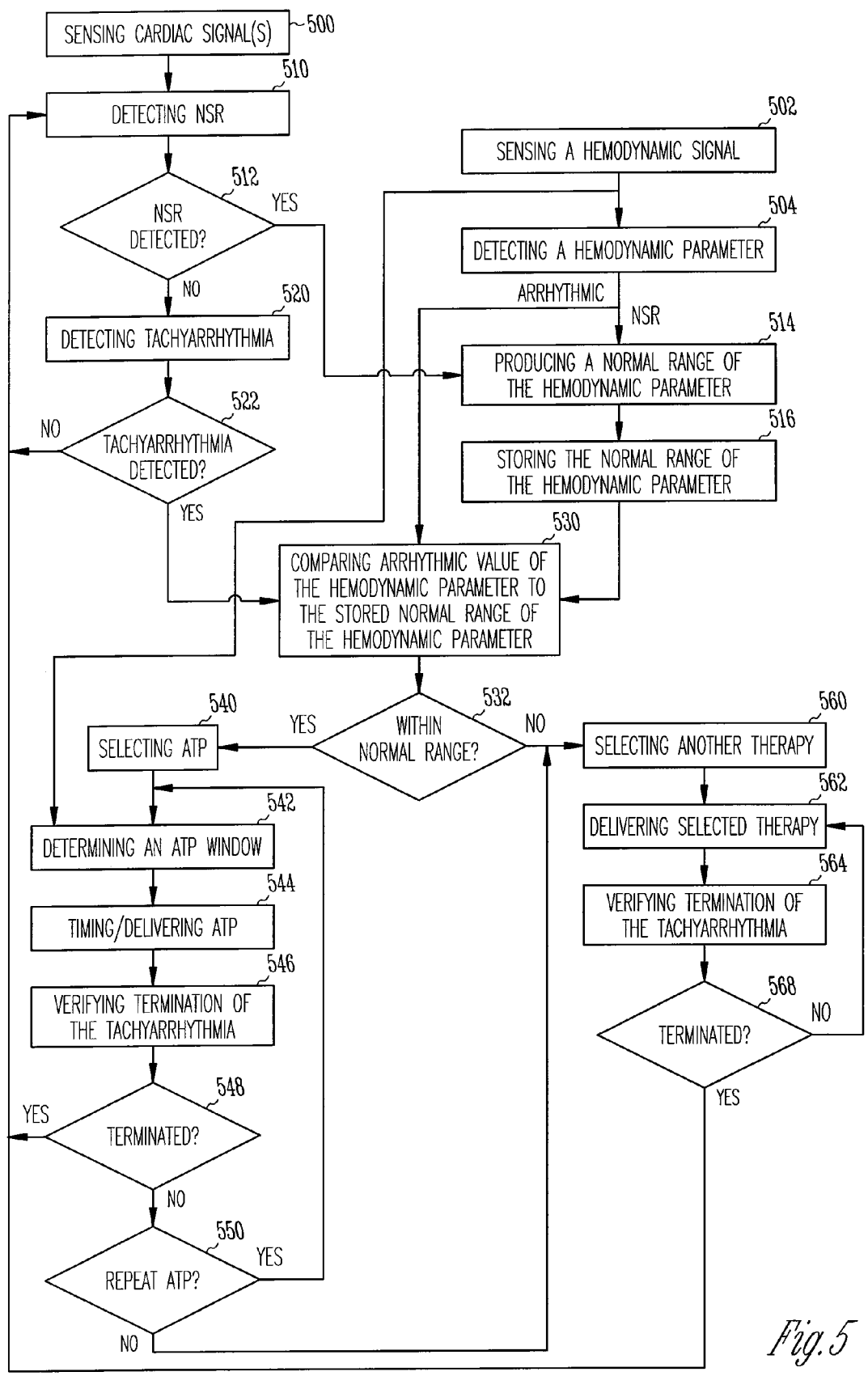
FIG. 5 is a flow chart illustrating an embodiment of a method for controlling ATP using a hemodynamic signal.

FIG. 5 is a flow chart illustrating an embodiment of a method for controlling ATP using a hemodynamic signal. In one embodiment, the method is performed by system 100, which includes hemodynamic sensor-controlled anti-tachyarrhythmia system 120, including its various embodiments discussed in this document.

One or more cardiac signals are sensed at 500. Examples of the one or more cardiac signals include atrial and ventricular electrograms. A hemodynamic signal indicative of hemodynamic performance is sensed at 502. Examples of the hemodynamic signal include a heart sound signal, an arterial pressure signal, and an impedance signal. A hemodynamic parameter is detected from the hemodynamic signal at 504. Examples of the hemodynamic parameter include an S2 amplitude being a voltage or energy amplitude related to S2, an arterial pressure measured at a predetermined point of the arterial pressure signal, and an impedance measured at a predetermined point of the impedance signal.

NSR is being detected at 510. In one embodiment, a detection of NSR is indicated when the one or more cardiac signals indicate a cardiac cycle length that falls within a predetermined NSR window and meets a minimum stability criterion. If the detection of NSR is indicated at 512, a normal range of the hemodynamic parameter is produced using a plurality of NSR values of the hemodynamic parameter detected during the NSR at 514. In one embodiment, the normal range of the hemodynamic parameter is produced using Equation [1]. In one embodiment, the plurality of values of the hemodynamic parameter includes about 15 values. The normal range of the hemodynamic parameter is stored at 516. In one embodiment, steps 514 and 516 are repeated on a regular basis, such as on a substantially periodic basis, when the detection of NSR is indicated at 512, such that the normal range of the hemodynamic parameter is updated to reflect a patient's changing physiologic conditions and metabolic needs. In another embodiment, steps 514 and 516 are repeated as needed, such as determined by a physician or other caregiver.

If the NSR is not detected at 512, tachyarrhythmia is being detected at 520. In one embodiment, tachyarrhythmia is detected using a ventricular electrogram. Ventricular depolarizations (R waves) are detected from the ventricular electrogram. Ventricular intervals (RR intervals) each being a time interval between two consecutively detected ventricular depolarizations are detected. A cardiac cycle length is calculated by averaging a predetermined number of the detected ventricular intervals. A detection of a tachyarrhythmia episode is indicated at 522 if the cardiac cycle length is shorter than a predetermined tachyarrhythmia threshold cycle length.

If the detection of the tachyarrhythmia episode is indicated at 522, an arrhythmic value of the hemodynamic parameter detected during the tachyarrhythmia episode is compared to the stored normal range of the hemodynamic parameter at 530. If the arrhythmic value of the hemodynamic parameter is within the stored normal range of the hemodynamic parameter at 532, ATP is selected at 540. If the arrhythmic value of the hemodynamic parameter is outside the stored normal range of the hemodynamic parameter at 532, another therapy, which is more aggressive, such as a defibrillation therapy, or a pacing/defibrillation therapy using the ATP-before-charge algorithm as discussed in U.S. patent application Ser. No. 10/817,751, is selected at 560.

If ATP is selected at 540, an ATP window is determined at 542. The ATP window is a time interval during which a delivery of ATP pulses is to be initiated. The beginning point (T1) of the ATP window is located by using a predetermined type characteristic feature detected from the hemodynamic signal. The predetermined type characteristic feature is temporally associated with the closure of the aortic valve and the closure of the pulmonary valve during each cardiac cycle. The end point (T2) of the ATP window is before the beginning of the ventricular depolarization (R wave). In one embodiment, the predetermined type characteristic feature is selected as the beginning point (T1) of the ATP window. In another embodiment, the beginning point (T1) of the ATP window is located using the predetermined type characteristic feature and an arrhythmia cycle length being the cardiac cycle length detected during the detected tachyarrhythmia episode. In a specific embodiment, the beginning point (T1) of the ATP window is selected from the predetermined type characteristic feature and the end of a timing interval in a cardiac cycle, whichever occurs later. The timing interval starts with a ventricular depolarization and is a predetermined percentage of the arrhythmia cycle length. In another embodiment, the beginning point (T1) of the ATP window is located using the predetermined type characteristic feature, the arrhythmia cycle length, and a parameter related to a relative stability of the arrhythmic cycle length. In a specific embodiment, the relative stability of the ventricular intervals used to calculate the arrhythmia cycle length is analyzed to produce the parameter related to heart rate stability as a function of the variance of the ventricular intervals. In locating the beginning point (T1) of the ATP window, more weight is given to the predetermined type characteristic feature, and less weight is given to the arrhythmia cycle length, when the relative stability of the arrhythmic cycle length decreases.

The ATP is timed and delivered at 544. The delivery of the ATP is initiated at the end of an ATP interval (T), which starts from the beginning point (T1) of the ATP window. In one embodiment, the delivery of the ATP includes the delivery of at least one burst of pacing pulses. The leading pacing pulse is delivered when the ATP interval (T) expires (at T1+T). Termination of the tachyarrhythmia episode, i.e., effectiveness of the ATP delivered at 544, is verified at 546. If the ATP fails to terminate the tachyarrhythmia episode at 548, and if the ATP is to be repeated according to a predetermined anti-tachyarrhythmia therapy strategy at 550, steps 542-550 are repeated. If the ATP fails to terminate the tachyarrhythmia episode at 548, but the ATP is not to be repeated according to a predetermined anti-tachyarrhythmia therapy strategy at 550, a more aggressive therapy is selected at 560.

If the more aggressive therapy is selected at 560, the selected therapy is delivered at 562. Termination of the tachyarrhythmia episode, i.e., effectiveness of the selected therapy delivered at 562, is verified at 564. If the selected therapy fails to terminate the tachyarrhythmia episode at 568, steps 562-568 are repeated until the tachyarrhythmia episode is terminated.

In one embodiment, multiple hemodynamic signals are sensed at 502. Steps 504, 514, 516, and 530 are performed concurrently and independently for each of the hemodynamic signals. A therapy selection algorithm applies a predetermined fusion method that uses the results of comparisons each performed with respect to one of the hemodynamic signals at step 532 to determine whether to select ATP at 540 or another therapy at 560. If the ATP is selected at 540, an algorithm for locating the ATP window applies a predetermined fusion method that uses predetermined type characteristic features each detected from one of the hemodynamic signals to locate at least the beginning point (T1) of the ATP window.

Specific embodiments of hemodynamic sensor-controlled anti-tachyarrhythmia system 420 are discussed below, with reference to FIGS. 6-9. In various embodiments, system 100 includes system elements each being any embodiment or combination of embodiments discussed in this document.

EXAMPLE 1

ATP Control Using Second Heart Sound (S2)

Figure 6:
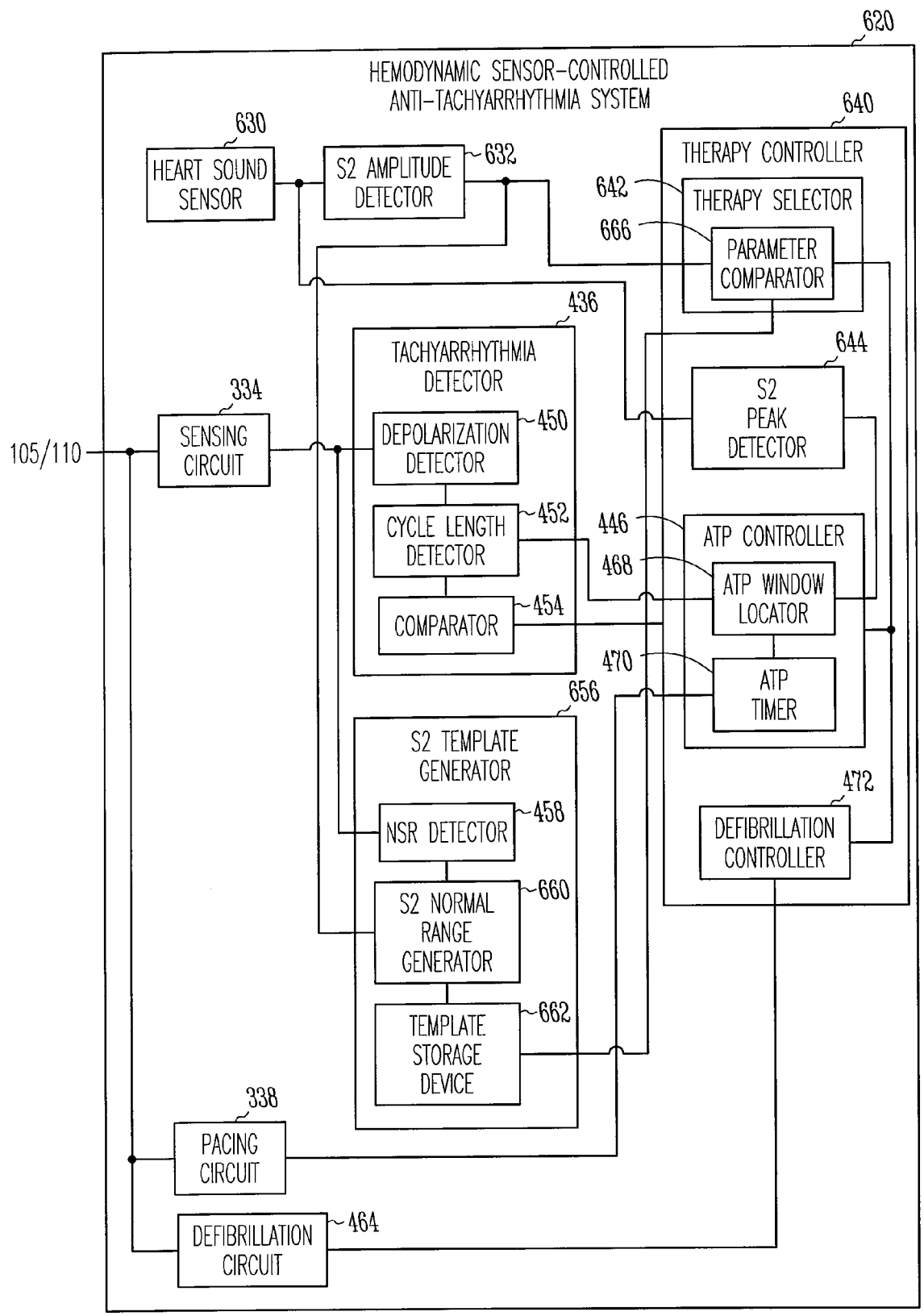
FIG. 6 is a block diagram illustrating an embodiment of a hemodynamic sensor-controlled anti-tachyarrhythmia system including a heart sound sensor.

FIG. 6 is a block diagram illustrating an embodiment of a hemodynamic sensor-controlled anti-tachyarrhythmia system 620, which is a specific embodiment of system 420. In this embodiment, the hemodynamic signal is a heart sound signal, the hemodynamic parameter is an S2 amplitude being the voltage amplitude of an S2 peak or the energy content of an occurrence of S2, and the predetermined type characteristic feature is the S2 peak. System 620 includes a heart sound sensor 630, an S2 amplitude detector 632, sensing circuit 334, tachyarrhythmia detector 436, pacing circuit 338, defibrillation circuit 464, an S2 template generator 656, and a therapy controller 640.

Heart sound sensor 630 senses a heart sound signal being a signal indicative of at least second heart sounds (S2). Examples of heart sound sensor 630 include an implantable accelerometer and an implantable microphone, each included in implantable medical device 101 or incorporated into lead 105 or lead 110. S2 amplitude detector 632 detects an S2 amplitude from the heart sound signal. Examples of the S2 amplitude include a peak voltage amplitude measured at one or more S2 peaks and an S2 energy amplitude representing the energy content of each occurrence of S2.

S2 template generator 656 includes NSR detector 458, an S2 normal range generator 660, and a template storage device 662. S2 normal range generator 660 receives NSR values of the S2 amplitude detected while the NSR is detected and produces a normal range of the S2 amplitude based on a plurality of the NSR values of the S2 amplitude. In one embodiment, normal range generator 660 produces the normal range using Equation [1], with $|X|_{AVG}$ being the average value of the S2 amplitude calculated using the plurality of the NSR values of the S2 amplitude, $|X|_{SD}$ being the standard deviation of the S2 amplitude calculated using the plurality of the NSR values of the S2 amplitude, and k being a predetermined constant associated with S2. In a specific embodiment, the plurality of the NSR values of the S2 amplitude includes approximately 15 NSR values. Template storage device 662 stores the normal range of the S2 amplitude.

Therapy controller 640 includes a therapy selector 642, an S2 peak detector 644, ATP controller 446, and defibrillation controller 472. Therapy selector 642 includes a parameter comparator 666 that compares an arrhythmic value of the S2 amplitude detected during the detected tachyarrhythmia episode to the stored normal range of the S2 amplitude. If the arrhythmic value of the S2 amplitude falls within the stored normal range of the S2 amplitude, therapy selector selects the ATP algorithm. If the arrhythmic value of the S2 amplitude is out of the stored normal range of the S2 amplitude, therapy selector 642 selects the cardioversion/defibrillation algorithm or the ATP-before-charge algorithm. S2 peak detector 644 detects S2 peaks from the heart sound signal. ATP window locator 468 uses at least an S2 peak in locating the beginning point (T1) of the ATP window. In one embodiment, S2 peak detector 644 also detects S2 and/or S2 peaks for S2 normal range generator 660 to measure the S2 amplitude from the S2 and/or S2 peaks. In various embodiments, S2 peak detector 644 includes an S2 detector to detect occurrences of S2. In a specific embodiment, the S2 detector includes an energy-based S2 detector that produces a heart sound envelogram using an envelope detector. The occurrences of S2 are detected using a threshold amplitude and timing information with respect to ventricular depolarizations (R waves) and/or occurrences of first heart sound (S1). In another embodiment, the S2 detector includes a correlation-based S2 detector that analyzes the correction between a segment of the heart sound signal and a predetermined S2 morphological template. Each occurrence of S2 is detected when the segment of the heart sound signal and the predetermined S2 morphological template substantially correlate. In another embodiment, the S2 detector includes a subspace S2 detector that detects the occurrences of S2 with blind source separation using independent component analysis.

Under some circumstances, detection of the S2 peak in the cardiac cycle during which the beginning point (T1) of the ATP window is to be located may be difficult. For example, the ATP interval (T) may be short when compared to the required computation time. Therefore, in one embodiment, S2 peak detector 644 uses a regression-based method to predict the location of the S2 peak that is directly used for locating the beginning point (T1) of the ATP window. Ventricular depolarizations (R waves) and occurrences of S2 are detected, from which ventricular intervals (RR intervals) and intervals each between a ventricular depolarization and an adjacent S2 peak ($RS_2$ intervals) are produced, during NSR. An $RS_2$-RR regression curve is constructed based on least square criterion. During the detected tachyarrhythmia episode, before the ATP delivery, locations of the detected S2 peaks are used to update the $RS_2$-RR regression curve. When the ATP is to be delivered, the location of the next S2 peak is predicted using the updated $RS_2$-RR regression curve and the location of the latest ventricular depolarization (R wave). The predicted location of the S2 peak is used in locating the beginning point (T1) of the ATP window.

EXAMPLE 2

ATP Control Using Pulmonary Arterial Pressure

Figure 7:
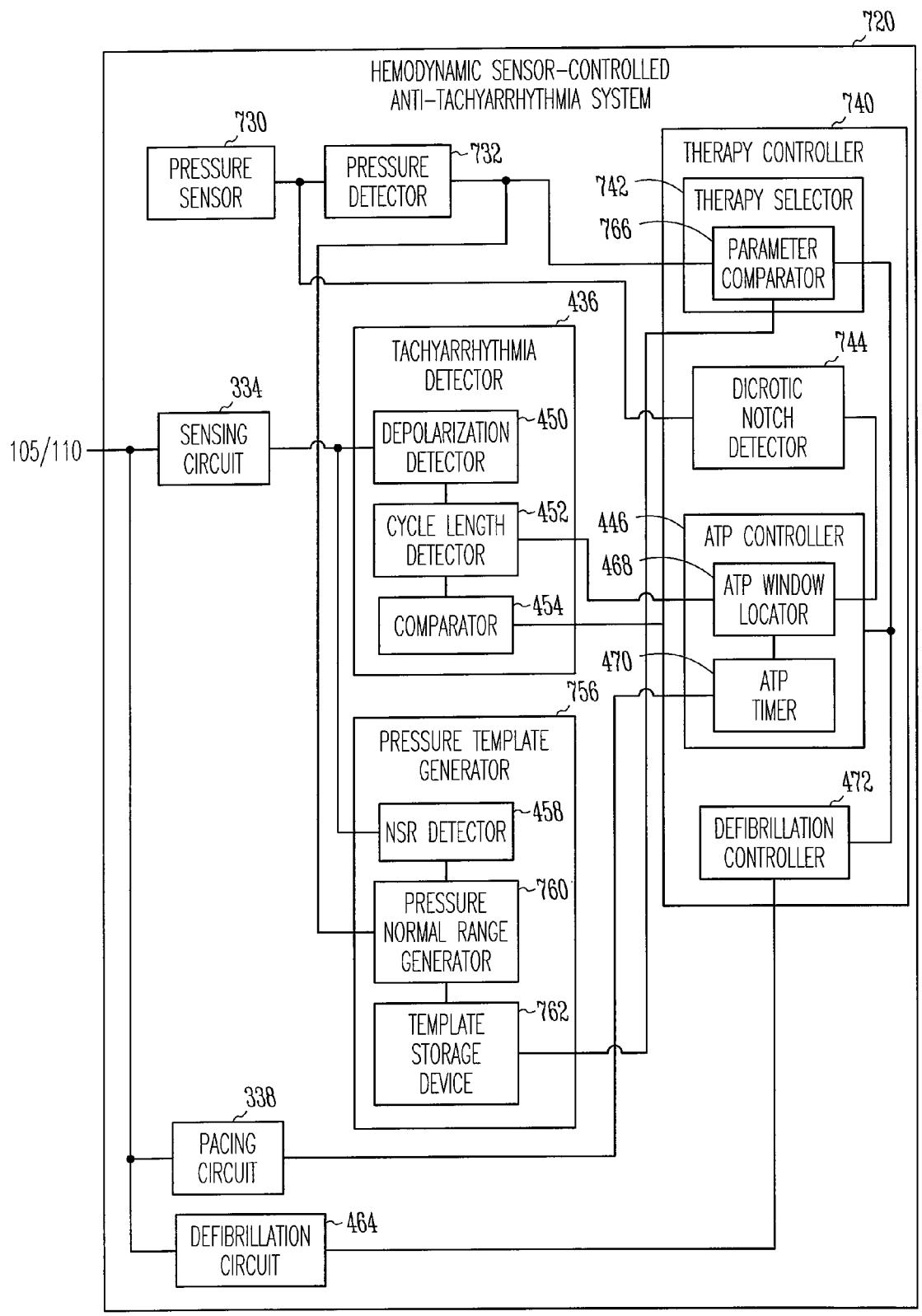
FIG. 7 is a block diagram illustrating an embodiment of a hemodynamic sensor-controlled anti-tachyarrhythmia system including an arterial pressure sensor.

FIG. 7 is a block diagram illustrating an embodiment of a hemodynamic sensor-controlled anti-tachyarrhythmia system 720, which is another specific embodiment of system 420. In this embodiment, the hemodynamic signal is an arterial pressure signal, the hemodynamic parameter is an arterial pressure measured from the arterial pressure signal, and the predetermined type characteristic feature is the dicrotic notch. System 720 includes a pressure sensor 730, a pressure detector 732, sensing circuit 334, tachyarrhythmia detector 436, pacing circuit 338, defibrillation circuit 464, a pressure template generator 756, and a therapy controller 740.

Arterial pressure sensor 730 senses an arterial pressure signal. Examples of arterial pressure sensor 730 include an implantable aortic pressure sensor that senses an aortic pressure signal and an implantable pulmonary artery pressure sensor that senses a pulmonary artery pressure signal. Pressure detector 732 detects the arterial pressure from the arterial pressure signal. In one embodiment, the arterial pressure is the amplitude of the arterial pressure signal measured at a predetermined point of a cardiac cycle. In another embodiment, the arterial pressure is an arterial pulse pressure measured as the peak-to-peak amplitude of the arterial pressure signal over a cardiac cycle.

Pressure template generator 756 includes NSR detector 458, a pressure normal range generator 760, and a template storage device 762. Pressure normal range generator 760 receives NSR values of the arterial pressure detected while the NSR is detected and produces a normal range of the arterial pressure based on a plurality of the NSR values of the arterial pressure. In one embodiment, pressure normal range generator 760 produces the normal range using Equation [1], with $|X|_{AVG}$ being the average value of the arterial pressure calculated using the plurality of the NSR values of the arterial pressure, $|X|_{SD}$ being the standard deviation of the arterial pressure calculated using the plurality of the NSR values of the arterial pressure, and k being a predetermined constant given for the arterial pressure, In a specific embodiment, the plurality of the NSR values of the arterial pressure includes approximately 15 NSR values. Template storage device 762 stores the normal range of the arterial pressure.

Therapy controller 740 includes a therapy selector 742, a dicrotic notch detector 744, ATP controller 446, and defibrillation controller 472. Therapy selector 742 includes a parameter comparator 766 that compares an arrhythmic value of the arterial pressure detected during the detected tachyarrhythmia episode to the stored normal range of the arterial pressure. If the arrhythmic value of the arterial pressure falls within the stored normal range of the arterial pressure, therapy selector 742 selects the ATP algorithm. If the arrhythmic value of the arterial pressure is out of the stored normal range of the arterial pressure, therapy selector 742 selects the cardioversion/defibrillation algorithm or the ATP-before-charge algorithm. Dicrotic notch detector 744 detects dicrotic notches from the arterial pressure signal. In one embodiment, dicrotic notch detector 744 produces a derivative signal being a first derivative of the arterial pressure signal and detects the dicrotic notches by comparing the derivative signal to a predetermined threshold. ATP window locator 468 uses at least one dicrotic notch in locating the beginning point (T1) of the ATP window.

Under some circumstances, detection of the dicrotic notch in the cardiac cycle during which the beginning point (T1) of the ATP window is to be located may be difficult. For example, the ATP interval (T) may be short when compared to the required computation time. Therefore, in one embodiment, dicrotic notch detector 644 uses a regression-based method to predict the location of the dicrotic notch that is directly used for locating the beginning point (T1) of the ATP window. Ventricular depolarizations (R waves) and dicrotic notches (D) are detected, from which ventricular intervals (RR intervals) and intervals each between a ventricular depolarization and an adjacent dicrotic notch (RD intervals) are produced, during NSR. An RD-RR regression curve is constructed based on least square criterion. During the detected tachyarrhythmia episode, before the ATP delivery, locations of the detected dicrotic notches are used to update the RD-RR regression curve. When the ATP is to be delivered, the location of the next dicrotic notch is predicted using the updated RD-RR regression curve and the location of the latest ventricular depolarization (R wave). The predicted location of the dicrotic notch is used in locating the beginning point (T1) of the ATP window.

EXAMPLE 3

ATP Control Using Impedance

Figure 8:
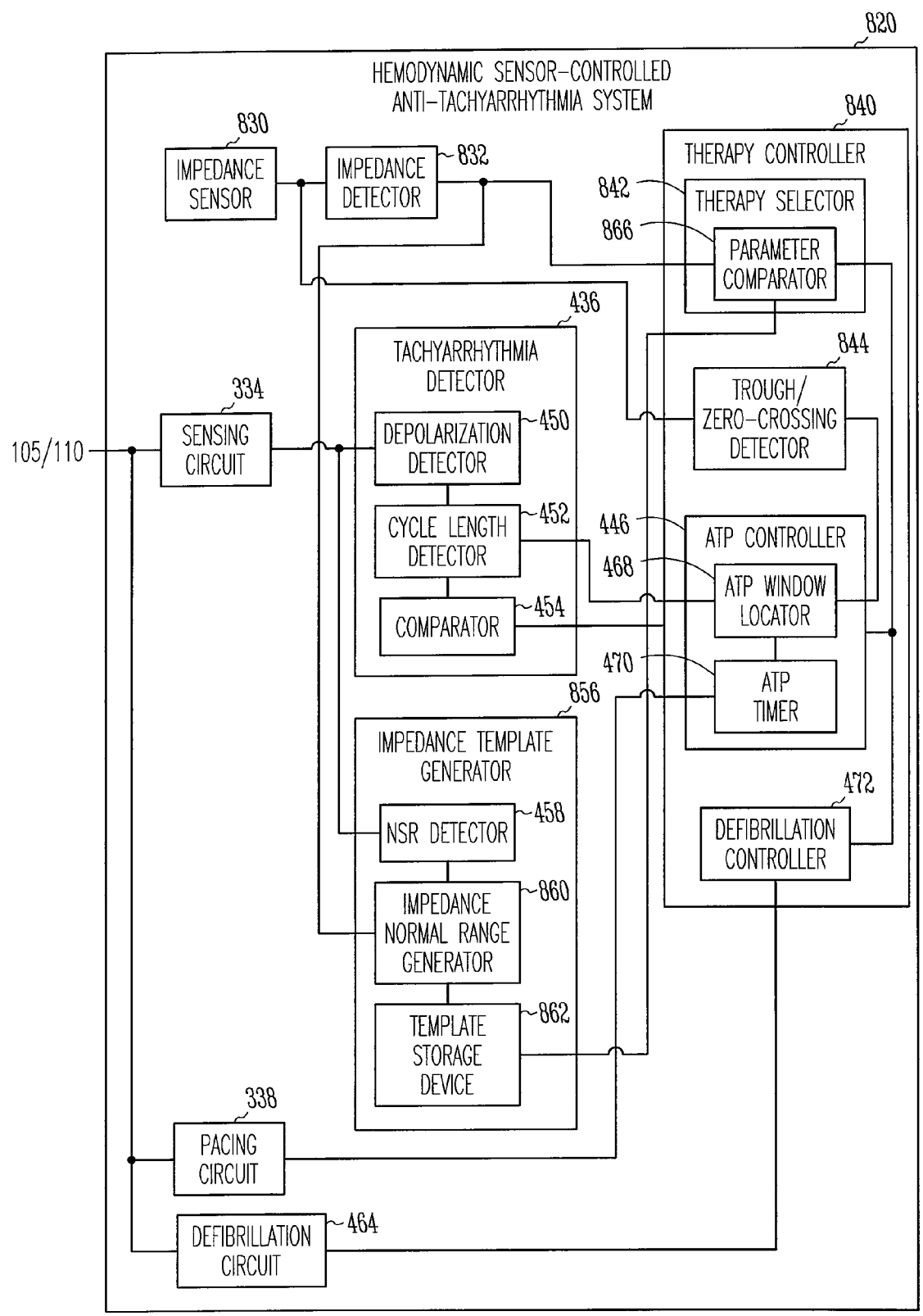
FIG. 8 is a block diagram illustrating an embodiment of a hemodynamic sensor-controlled anti-tachyarrhythmia system including an impedance sensor.

FIG. 8 is a block diagram illustrating an embodiment of a hemodynamic sensor-controlled anti-tachyarrhythmia system 820, which is another specific embodiment of system 420. In this embodiment, the hemodynamic signal is an impedance signal (Z), the hemodynamic parameter is an impedance measured from the impedance signal, and the predetermined type characteristic feature is a trough point of the first derivative of the impedance signal (dZ/dt) or a zero-crossing point of the second derivative of the impedance signal ($d^2Z/dt^2$). In one embodiment, the impedance signal (Z) is a thoracic impedance signal. In another embodiment, the impedance signal (Z) is a cardiac impedance signal. System 820 includes an impedance sensor 830, an impedance detector 832, sensing circuit 334, tachyarrhythmia detector 436, pacing circuit 338, defibrillation circuit 464, an impedance template generator 856, and a therapy controller 840.

Impedance sensor 830 senses an impedance signal. Impedance detector 832 detects the impedance from the impedance signal. In one embodiment, the impedance is the amplitude of the impedance signal measured at a predetermined point of a cardiac cycle. In another embodiment, the impedance is a pulse impedance measured as the peak-to-peak amplitude of the impedance over a cardiac cycle.

Impedance template generator 856 includes NSR detector 458, an impedance normal range generator 860, and a template storage device 862. Impedance normal range generator 860 receives NSR values of the impedance detected while the NSR is detected and produces a normal range of the impedance based on a plurality of the NSR values of the impedance. In one embodiment, impedance normal range generator 860 produces the normal range using Equation [1], with $|X|_{AVG}$ being the average value of the impedance calculated using the plurality of the NSR values of the impedance, $|X|_{SD}$ being the standard deviation of the impedance calculated using the plurality of the NSR values of the impedance, and k being a predetermined constant given for the impedance, In a specific embodiment, the plurality of the NSR values of the impedance includes approximately 15 NSR values. Template storage device 862 stores the normal range of the impedance.

Therapy controller 840 includes a therapy selector 842, a trough/zero-crossing detector 844, ATP controller 446, and defibrillation controller 472. Therapy selector 842 includes a parameter comparator 866 that compares an arrhythmic value of the impedance detected during the detected tachyarrhythmia episode to the stored normal range of the impedance. If the arrhythmic value of the impedance falls within the stored normal range of the impedance, therapy selector 842 selects the ATP algorithm. If the arrhythmic value of the impedance is out of the stored normal range of the impedance, therapy selector 842 selects the cardioversion/defibrillation algorithm or the ATP-before-charge algorithm. Trough/zero-crossing detector 844 detects a trough point from a signal being the first derivative of the impedance signal (dZ/dt) and/or a zero-crossing point from a signal being the second derivative of the impedance signal ($d^2Z/dt^2$). ATP window locator 468 uses at least one of the trough point and the zero-crossing point in locating the beginning point (T1) of the ATP window.

Under some circumstances, detection of the trough or zero-crossing point in the cardiac cycle during which the beginning point (T1) of the ATP window is to be located may be difficult. For example, the ATP interval (T) may be short when compared to the required computation time. Therefore, in one embodiment, trough/zero-crossing detector 844 uses a regression-based method to predict the location of the trough or zero-crossing point that is directly used for locating the beginning point (T1) of the ATP window. Ventricular depolarizations (R waves) and trough or zero-crossing points (Z) are detected, from which ventricular intervals (RR intervals) and intervals each between a ventricular depolarization and an adjacent trough or zero-crossing point (RZ intervals) are produced, during NSR. An RZ-RR regression curve is constructed based on least square criterion. During the detected tachyarrhythmia episode, before the ATP delivery, locations of the detected trough or zero-crossing points are used to update the RZ-RR regression curve. When the ATP is to be delivered, the location of the next trough or zero-crossing point is predicted using the updated RZ-RR regression curve and the location of the latest ventricular depolarization (R wave). The predicted location of the trough or zero-crossing point is used in locating the beginning point (T1) of the ATP window.

EXAMPLE 4

ATP Control Using Multiple Hemodynamic Signals

Figure 9:
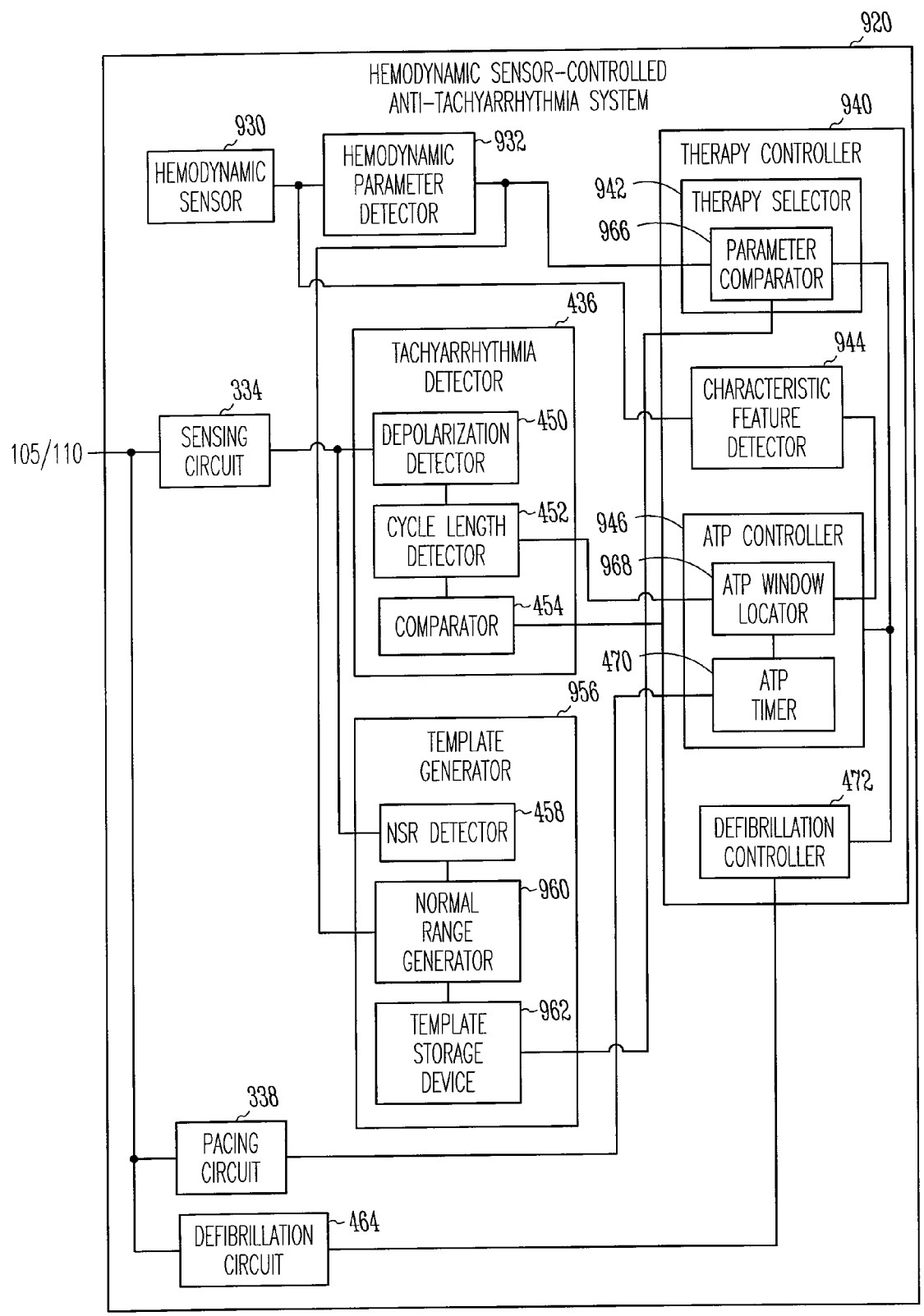
FIG. 9 is a block diagram illustrating an embodiment of a hemodynamic sensor-controlled anti-tachyarrhythmia system including multiple hemodynamic sensors.

FIG. 9 is a block diagram illustrating an embodiment of a hemodynamic sensor-controlled anti-tachyarrhythmia system 920, which is another specific embodiment of system 420. In this embodiment, two or more hemodynamic signals are sensed and processed for controlling whether and/or when to deliver the ATP. Examples of the two or more hemodynamic signals include the heart sound signal, the arterial pressure signal, and the impedance signal discussed above. System 920 includes hemodynamic sensors 930, hemodynamic parameter detector 932, sensing circuit 334, tachyarrhythmia detector 436, pacing circuit 338, defibrillation circuit 464, a template generator 956, and a therapy controller 940. In a specific embodiment, system 920 is a combination of two or more of systems 620, 720, and 820, with the selection and/or the timing of the ATP therapy controlled using two or more of the heart sound signal, the arterial pressure signal, and the impedance signal. Such a system increases the robustness of therapy control because, for example, the performance of each type of sensor varies from patient to patient.

Hemodynamic sensors 930 includes a plurality of hemodynamic sensors to sense a plurality of hemodynamic signals each being a signal indicative of hemodynamic performance. In one embodiment, hemodynamic sensors 930 include two or more of heart sound sensor 630, pressure sensor 730, and impedance sensor 830.

Hemodynamic parameter detector 932 detects hemodynamic parameters each from one of the hemodynamic signals. In one embodiment, hemodynamic parameter detector 932 includes two or more of S2 amplitude detector 632, pressure detector 732, and impedance detector 832.

Template generator 956 produces a normal range for each of the hemodynamic parameters and includes NSR detector 458, a normal range detector 960, and a template storage device 962. In one embodiment, template generator 956 includes two or more of S2 template generator 656, pressure template generator 756, and impedance template generator 856. Normal range generator 960 includes corresponding two or more of S2 normal range generator 660, pressure normal range generator 760, and impedance normal range generator 860. Template storage device 962 stores the normal range of each of the hemodynamic parameters produced by normal range generator 960.

Therapy controller 940 includes a therapy selector 942, a characteristic feature detector 944, an ATP controller 946, and defibrillation controller 472. Therapy selector 942 includes a parameter comparator 966 that compares an arrhythmic value of each of the hemodynamic parameters detected during the tachyarrhythmia episode to the stored normal range of that hemodynamic parameter. The decision of whether to select the ATP algorithm is made by applying a predetermined fusion method using the results each from a comparison between the arrhythmic value of one of the hemodynamic parameters and the stored normal range of that hemodynamic parameter. In one embodiment, therapy selector 942 selects the ATP algorithm when the arrhythmic value of every hemodynamic parameter falls within the stored normal range of that hemodynamic parameter.

Characteristic feature detector 944 detects predetermined type characteristic features from each of the hemodynamic signals. The predetermined type characteristic features are each temporally associated with the closure of the aortic valve and the closure of the pulmonary valve in a cardiac cycle. Examples of the predetermined type characteristic features include the S2 peak in the heart sound signal, the dicrotic notch in the arterial pressure signal, the trough point in the first derivative of the impedance signal, and the zero-crossing point in the second derivative of the impedance signal.

ATP controller 946 controls the timing of the delivery of ATP pulses using the detected predetermined type characteristic features and includes an ATP window locator 968 and ATP timer 470. ATP window locator 968 locates the beginning point (T1) of the ATP window using the locations of the detected predetermined type characteristic features. In one embodiment, the beginning point (T1) of the ATP window is located using each of the hemodynamic signals by using the method performed by ATP window locator 468. The results are applied in a predetermined fusion method that produces the beginning point (T1) of the ATP window that is directly used for the delivery of the ATP pulses. In one embodiment, ATP window locator 968 identifies the median of T1s produced from all the hemodynamic signals to use as the beginning point (T1) of the ATP window. In another embodiment, ATP window locator 968 identifies the longest (latest) T1 produced from all the hemodynamic signals to use as the beginning point (T1) of the ATP window.

In General

It is to be understood that the above detailed description is intended to be illustrative, and not restrictive. For example, any hemodynamic or other physiological signal that includes a detectable feature having a known or predictable temporal relationship with the excitable gap of the reentrant loop associated with tachyarrhythmia, besides those specifically discussed in this document, is useable in locating the beginning point (T1) of the ATP window. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management (CRM) system, comprising:
 a sensing circuit to sense at least one cardiac signal;
 a tachyarrhythmia detector, coupled to the sensing circuit, to detect a cardiac cycle length from the at least one cardiac signal and detect a tachyarrhythmia episode using the detected cardiac cycle length;
 a hemodynamic sensor to sense a hemodynamic signal indicative of hemodynamic performance;
 a hemodynamic parameter detector, coupled to the hemodynamic sensor, to detect a hemodynamic parameter from the hemodynamic signal;
 a pacing circuit to deliver pacing pulses;
 a therapy controller coupled to the tachyarrhythmia detector, the hemodynamic parameter detector, and the pacing circuit, the therapy controller including:

a therapy selector adapted to compare an arrhythmic value of the hemodynamic parameter detected during the detected tachyarrhythmia episode to a normal range of the hemodynamic parameter and to select an anti-tachyarrhythmia pacing (ATP) algorithm in response to the arrhythmic value of the hemodynamic parameter falling within the normal range of the hemodynamic parameter and a cardioversion/defibrillation algorithm in response to the arrhythmic value of the hemodynamic parameter falling out of the normal range of the hemodynamic parameter;

a characteristic feature detector adapted to detect a predetermined type morphological feature of the hemodynamic signal, the predetermined type morphological feature temporally associated with an aortic valve closure and a pulmonary valve closure; and an ATP controller, coupled to the therapy selector and the characteristic feature detector, to control the delivery of the pacing pulses by executing the selected ATP algorithm, the ATP controller adapted to select the detected predetermined type morphological feature as a beginning point of an ATP window and initiate a delivery of a burst of the pacing pulses within the ATP window to interrupt a reentrant loop causing the tachyarrhythmia.

2. The CRM system of claim 1, further comprising:
a template generator to produce the normal range of the hemodynamic parameter, the template generator including:
  an normal sinus rhythm (NSR) detector, coupled to the sensing circuit, to detect an NSR from the at least one cardiac signal; and
  a normal range generator coupled to the NSR detector and the hemodynamic parameter detector, the normal range generator adapted to receive a plurality of NSR values of the hemodynamic parameter detected while the NSR is detected and to produce the normal range of the hemodynamic parameter based on the plurality of NSR values of the hemodynamic parameter; and
  a template storage device, coupled to the normal range generator, to store the normal range of the hemodynamic parameter.

3. The CRM system of claim 2, wherein the normal range generator is adapted to produce the normal range using an equation: $|X|_{AVG} \pm k \cdot |X|_{SD}$, where $|X|_{AVG}$ is an average value of the hemodynamic parameter calculated using the plurality of NSR values of the hemodynamic parameter, $|X|_{SD}$ is a standard deviation of the hemodynamic parameter calculated using the plurality of NSR values of the hemodynamic parameter, and k is a predetermined constant.

4. The CRM system of claim 1, wherein the hemodynamic signal comprises a heart sound signal indicative of at least second heart sounds (S2), the hemodynamic parameter comprises an S2 amplitude, the hemodynamic sensor includes a heart sound sensor adapted to sense the heart sound signal, and the hemodynamic parameter detector comprises an amplitude detector to detect the S2 amplitude from the heart sound signal.

5. The CRM system of claim 1, wherein the hemodynamic signal comprises an arterial pressure signal, the hemodynamic parameter comprises an arterial pressure, the hemodynamic sensor comprises an arterial pressure sensor adapted to sense the arterial pressure signal, and the hemodynamic parameter detector comprises a pressure detector to detect the arterial pressure from the arterial pressure signal.

6. The CRM system of claim 1, wherein the hemodynamic signal comprises an impedance signal indicative of at least one of a thoracic impedance and a cardiac impedance, the hemodynamic parameter comprises an impedance, the hemodynamic sensor comprises an impedance sensor adapted to sense the impedance signal, and the hemodynamic parameter detector comprises an impedance detector to detect the impedance from the impedance signal.

7. A method for operating a cardiac rhythm management (CRM) device, the method comprising:
  sensing at least one cardiac signal;
  detecting a cardiac cycle length using the at least one cardiac signal;
  detecting a tachyarrhythmia episode using the detected cardiac cycle length;
  sensing a hemodynamic signal indicative of hemodynamic performance;
  detecting a hemodynamic parameter from the hemodynamic signal;
  producing an arrhythmic value of the hemodynamic parameter being a value of the hemodynamic parameter detected during the detected tachyarrhythmia episode;
  comparing the arrhythmic value of the hemodynamic parameter to a normal range of the hemodynamic parameter;
  selecting anti-tachyarrhythmia pacing (ATP) in response to the arrhythmic value of the hemodynamic parameter falling within the normal range of the hemodynamic parameter and a cardioversion/defibrillation algorithm in response to the arrhythmic value of the hemodynamic parameter falling out of the normal range of the hemodynamic parameter;
  detecting a predetermined type morphological feature of the hemodynamic signal the predetermined type morphological feature temporally associated with an aortic valve closure and a pulmonary valve closure;
  selecting the predetermined type morphological feature as a beginning point of an ATP window; and
  initiating a delivery of a burst of ATP pulses within the ATP window to interrupt a reentrant loop causing the tachyarrhythmia.

8. The method of claim 7, further comprising:
  detecting a normal sinus rhythm (NSR) from the at least one cardiac signal; and
  producing the normal range of the hemodynamic parameter using a plurality of NSR values of the hemodynamic parameter each being a value of the hemodynamic parameter detected during the NSR.

9. The method of claim 8, wherein producing the normal range of the hemodynamic parameter comprises producing the normal range using an equation: $|X|_{AVG} \pm k \cdot |X|_{SD}$, where $|X|_{AVG}$ is an average value of the hemodynamic parameter calculated using the plurality of NSR values of the hemodynamic parameter, $|X|_{SD}$ is a standard deviation of the hemodynamic parameter calculated using the plurality of NSR values of the hemodynamic parameter, and k is a predetermined constant.

10. The method of claim 7, wherein sensing the hemodynamic signal comprises sensing a heart sound signal indicative of at least second heart sounds (S2), and detecting the hemodynamic parameter from the hemodynamic signal comprises detect an S2 amplitude from the heart sound signal.

11. The method of claim 7, wherein sensing the hemodynamic signal comprises sensing an arterial pressure signal, and detecting the hemodynamic parameter from the hemodynamic signal comprises detecting an arterial pressure from the arterial pressure signal.

12. The method of claim 7, wherein sensing the hemodynamic signal comprises sensing an impedance signal indicative of at least one of a thoracic impedance and a cardiac impedance, and detecting the hemodynamic parameter from the hemodynamic signal comprises detecting an impedance from the impedance signal.

13. A cardiac rhythm management (CRM) system, comprising:
   a sensing circuit to sense at least one cardiac signal;
   a tachyarrhythmia detector, coupled to the sensing circuit, to detect a tachyarrhythmia episode from the at least one cardiac signal;
   a hemodynamic sensor to sense a hemodynamic signal indicative of hemodynamic performance;
   a pacing circuit to deliver pacing pulses;
   a therapy controller coupled to the tachyarrhythmia detector, the hemodynamic sensor, and the pacing circuit, the therapy controller including:
      a characteristic feature detector adapted to detect a predetermined type characteristic feature of the hemodynamic signal, the predetermined type characteristic feature being a morphological feature temporally associated with an aortic valve closure and a pulmonary valve closure; and
      an anti-tachyarrhythmia pacing (ATP) controller coupled to the characteristic feature detector, the ATP controller adapted to select the detected predetermined type morphological feature as a beginning point of an ATP window and initiate a delivery of a burst of the pacing pulses within the ATP window.

14. The CRM system of claim 13, wherein the hemodynamic signal comprises a heart sound signal indicative of at least second heart sounds (S2), the predetermined type characteristic feature comprises a peak of S2, the hemodynamic sensor includes a heart sound sensor adapted to sense the heart sound signal, and the characteristic feature detector comprises an S2 peak detector adapted to detect the peak of S2 from the heart sound signal.

15. The CRM system of claim 13, wherein the hemodynamic signal comprises an arterial pressure signal, the predetermined type characteristic feature comprises a dicrotic notch of the arterial pressure signal, the hemodynamic sensor comprises an arterial pressure sensor adapted to sense the arterial pressure signal, and the characteristic feature detector comprises a dicrotic notch detector adapted to detect the dicrotic notch.

16. The CRM system of claim 13, wherein the hemodynamic signal comprises an impedance signal (Z) indicative of at least one of a thoracic impedance and a cardiac impedance, the predetermined type characteristic features comprises a trough point of the first derivative of the impedance signal (dZ/dt), the hemodynamic sensor comprises an impedance sensor adapted to sense the impedance signal, and the characteristic feature detector is adapted to produce a signal being the first derivative of the impedance signal (dZ/dt) and to detect a trough point of the signal being the first derivative of the impedance signal (dZ/dt) in a cardiac cycle.

17. The CRM system of claim 13, wherein the hemodynamic signal comprises an impedance signal (Z) indicative of at least one of a thoracic impedance and a cardiac impedance, the predetermined type characteristic feature comprises a zero-crossing point of the second derivative of the impedance signal ($d^2Z/dt^2$), the hemodynamic sensor comprises an impedance sensor adapted to sense the impedance signal, and the characteristic feature detector is adapted to produce a signal being the second derivative of the impedance signal ($d^2Z/dt^2$) and to detect a zero-crossing point of the signal being the second derivative of the impedance signal ($d^2Z/dt^2$) in a cardiac cycle.

18. The CRM system of claim 13, wherein the ATP controller comprises an ATP window locator adapted to locate the beginning point of the ATP window; and
   an ATP timer, coupled to the ATP window locator, to time an ATP interval from the beginning point of the ATP window and initiate the delivery of the burst of the pacing pulses upon expiration of the ATP interval.

19. The CRM system of claim 18, wherein the therapy controller further comprises:
   a hemodynamic parameter detector, coupled to the hemodynamic sensor, to detect a hemodynamic parameter from the hemodynamic signal; and
   a therapy selector coupled to the hemodynamic parameter detector, the therapy selector adapted to compare an arrhythmic value of the hemodynamic parameter detected during the tachyarrhythmia episode to a normal range of the hemodynamic parameter and to select an ATP algorithm if the arrhythmic value of the hemodynamic parameter falls within the normal range of the hemodynamic parameter, and
   wherein the ATP controller is adapted to control the delivery of the pacing pulses by executing the selected ATP algorithm.

20. A method for operating a cardiac rhythm management (CRM) device, the method comprising:
   sensing at least one cardiac signal;
   detecting a tachyarrhythmia episode from the at least one cardiac signal;
   sensing a hemodynamic signal indicative of hemodynamic performance;
   detecting a predetermined type characteristic feature of the hemodynamic signal, the predetermined type characteristic feature being a morphological feature temporally associated with an aortic valve closure and a pulmonary valve closure;
   selecting the predetermined type morphological feature as a beginning point of an anti-tachyarrhythmia pacing (ATP) window; and
   initiating a delivery of a burst of ATP pulses within the ATP window to interrupt a reentrant loop causing the tachyarrhythmia.

21. The method of claim 20, wherein initiating the delivery of the burst of ATP pulses comprises:
   timing a predetermined ATP interval from the beginning point of the ATP window; and
   initiating the delivery of ATP when the ATP interval expires.

22. The method of claim 21, wherein sensing the hemodynamic signal comprises sensing a heart sound signal indicative of at least second heart sounds (S2), and detecting the predetermined type characteristic feature from the hemodynamic signal comprises detecting a peak of S2 from the heart sound signal.

23. The method of claim 21, wherein sensing the hemodynamic signal comprises sensing an arterial pressure signal, and detecting the predetermined type characteristic feature from the hemodynamic signal comprises detecting a dicrotic notch from the arterial pressure signal.

24. The method of claim 21, wherein sensing the hemodynamic signal comprises sensing an impedance signal (Z) indicative of at least one of a thoracic impedance and a cardiac impedance, and detecting the predetermined type characteristic feature from the hemodynamic signal comprises:
   producing a signal being the first derivative of the impedance signal (dZ/dt); and
   detecting a trough point of the signal being the first derivative of the impedance signal (dZ/dt) in a cardiac cycle.

25. The method of claim 21, wherein sensing the hemodynamic signal comprises sensing an impedance signal (Z) indicative of at least one of a thoracic impedance and a cardiac impedance, and detecting the predetermined type characteristic feature from the hemodynamic signal comprises:
- producing a signal being the second derivative of the impedance signal ($d^2Z/dt^2$); and
- detecting a zero-crossing point of the signal being the second derivative of the impedance signal ($d^2Z/dt^2$) in a cardiac cycle.

26. The method of claim 21, further comprising:
- detecting a hemodynamic parameter from the hemodynamic signal;
- comparing an arrhythmic value of the hemodynamic parameter detected during the tachyarrhythmia episode to a normal range of the hemodynamic parameter; and
- selecting an ATP algorithm if the arrhythmic value of the hemodynamic parameter falls within the normal range of the hemodynamic parameter, and
- wherein timing the delivery of ATP using the beginning point of the ATP window comprises timing the delivery of ATP by executing the selected ATP algorithm using the beginning point of the ATP window.

\* \* \* \* \*

UNITED STATES PATENT AND TRADEMARK OFFICE
CERTIFICATE OF CORRECTION

| | | |
|---|---|---|
| PATENT NO. | : 7,844,331 B2 | Page 1 of 1 |
| APPLICATION NO. | : 11/312082 | |
| DATED | : November 30, 2010 | |
| INVENTOR(S) | : Dan Li et al. | |

It is certified that error appears in the above-identified patent and that said Letters Patent is hereby corrected as shown below:

In column 20, line 32, in Claim 7, delete "signal" and insert -- signal, --, therefor.

In column 21, line 28, in Claim 13, delete "window." and insert -- window to interrupt a reentrant loop causing the tachyarrhythmia. --, therefor.

Signed and Sealed this
First Day of March, 2011

David J. Kappos
*Director of the United States Patent and Trademark Office*